US009952203B2

(12) United States Patent
Kay-Fedorov et al.

(10) Patent No.: US 9,952,203 B2
(45) Date of Patent: Apr. 24, 2018

(54) IMMUNE SUPPRESSOR AND ITS USE

(75) Inventors: Penelope Kay-Fedorov, Hannover (DE); Martin Messerle, Hannover (DE); Thomas F. Schulz, Hannover (DE); Lars Steinbrück, Hannover (DE); Ildar Gabaev, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 14/006,222

(22) PCT Filed: Mar. 21, 2012

(86) PCT No.: PCT/EP2012/054985
§ 371 (c)(1),
(2), (4) Date: Sep. 19, 2013

(87) PCT Pub. No.: WO2012/126940
PCT Pub. Date: Sep. 27, 2012

(65) Prior Publication Data
US 2014/0079725 A1    Mar. 20, 2014

(30) Foreign Application Priority Data
Mar. 22, 2011    (EP) .................................. 11159203

(51) Int. Cl.
| G01N 33/50 | (2006.01) |
| C07K 14/005 | (2006.01) |
| A61K 38/16 | (2006.01) |
| A61K 39/245 | (2006.01) |
| A61K 39/12 | (2006.01) |
| C12N 7/00 | (2006.01) |
| C07K 14/045 | (2006.01) |

(52) U.S. Cl.
CPC ......... *G01N 33/505* (2013.01); *A61K 38/162* (2013.01); *C07K 14/005* (2013.01); *G01N 33/5052* (2013.01); *C07K 2319/30* (2013.01); *C12N 2710/10041* (2013.01); *C12N 2710/16111* (2013.01); *C12N 2740/10041* (2013.01); *G01N 2333/045* (2013.01); *G01N 2333/70589* (2013.01); *G01N 2800/24* (2013.01)

(58) Field of Classification Search
CPC .............. A61K 2039/525; A61K 39/12; A61K 39/245; A61K 35/763; C12N 7/00; C12N 2710/16643; C12N 2710/16634; C12N 2710/16622; C12N 2710/16632; C12N 2710/16645; C12N 15/8695; C12N 2710/16034; C12N 2710/16662; C12N 15/869; C12N 2710/16032; C12N 2710/16111; C12N 2710/16122; C12N 2710/16134; C12N 2710/16141; C07K 14/005; C07K 14/045
See application file for complete search history.

(56) References Cited

U.S. PATENT DOCUMENTS

| 5,767,250 | A * | 6/1998 | Spaete ......................... 530/395 |
| 5,834,307 | A * | 11/1998 | Spaete et al. .............. 435/320.1 |
| 6,100,064 | A * | 8/2000 | Burke et al. ................. 435/69.3 |
| 7,553,932 | B1 * | 6/2009 | Von Herrath et al. ........ 530/351 |
| 7,892,822 | B1 * | 2/2011 | Koszinowski et al. ..... 435/320.1 |
| 2005/0064394 | A1* | 3/2005 | Liu et al. ........................... 435/5 |
| 2008/0102087 | A1* | 5/2008 | Vilalta et al. .............. 424/231.1 |
| 2011/0081365 | A1* | 4/2011 | Cortez et al. .............. 424/184.1 |
| 2012/0237546 | A1* | 9/2012 | Singh et al. ............... 424/211.1 |
| 2013/0065861 | A1* | 3/2013 | Wu et al. ...................... 514/119 |
| 2013/0101629 | A1* | 4/2013 | Skibinski et al. ............ 424/400 |

OTHER PUBLICATIONS

Brune W. UL11 [Human herpesvirus 5]. GenBank Acc. No: ABV71541.1. Dep. Oct. 30, 2007.*
Malouli D, Nakayasu ES, Viswanathan K, Camp DG 2nd, Chang WL, Barry PA, Smith RD, Früh K. Reevaluation of the coding potential and proteomic analysis of the BAC-derived rhesus cytomegalovirus strain 68-1. J Virol. Sep. 2012;86(17):8959-73. Epub Jun. 20, 2012.*
Mateu MG, et. al. Eur J Immunol. Jun. 1992;22(6):1385-9.*
Greenspan NS, Di Cera E. Defining epitopes: It's not as easy as it seems. Nat Biotechnol. Oct. 1999;17(10):936-7.*
Gabaev I, Steinbrück L, Pokoyski C, Pich A, Stanton RJ, Schwinzer R, Schulz TF, Jacobs R, Messerle M, Kay-Fedorov PC. The human cytomegalovirus UL11 protein interacts with the receptor tyrosine phosphatase CD45, resulting in functional paralysis of T cells. PLoS Pathog. Dec. 2011;7(12):e1002432. Epub Dec. 8, 2011.*
Sheng Y, Mancino V, Birren B. Transformation of *Escherichia coli* with large DNA molecules by electroporation. Nucleic Acids Res. Jun. 11, 1995;23(11):1990-6.*
Nicola AV, Willis SH, Naidoo NN, Eisenberg RJ, Cohen GH. Structure-function analysis of soluble forms of herpes simplex virus glycoprotein D. J Virol. Jun. 1996;70(6):3815-22.*
Lilley BN, Ploegh HL, Tirabassi RS. Human cytomegalovirus open reading frame TRL11/IRL11 encodes an immunoglobulin G Fc-binding protein. J Virol. Nov. 2001;75(22):11218-21.*
Brune W. Human herpesvirus 5 strain TB40/E clone TB40-BAC4, complete sequence. GenBank: EF999921.1. Dep. Oct. 30, 2007.*
Gabaev I, et. al. PLoS Pathog. Dec. 2011;7(12):e1002432. Epub Dec. 8, 2011. With Supplemental Figures.*

(Continued)

*Primary Examiner* — Rachel B Gill
(74) *Attorney, Agent, or Firm* — Whitham, Curtis & Cook, P.C.

(57) ABSTRACT

The present invention relates to a new binder molecule useful e.g. as an immune suppressor. In particular, it has been recognized that the UL11 protein of human the cytomegalovirus, binds to the CD45 molecule, potentially altering the immune system of an individual. In addition, the present invention relates to binder molecules, in particular, fusion molecules containing the CD45 binding domain of the UL11 protein in combination with a second molecule of interest for delivery of said molecule to cells expressing the CD45 molecule. Moreover, the present invention relates to pharmaceutical compositions comprising the UL11 protein of human cytomegalovirus, or derivatives or homologs thereof, or a nucleic acid sequence encoding the same.

8 Claims, 6 Drawing Sheets

(56) References Cited

OTHER PUBLICATIONS

Database UniProt, "SubName: Full-UL11", Jan. 15, 2008, web.
Sinzger et al., "Cloning and sequencing of a highly productive endotheliotropic virus strain derived from human cytomegalovirus TB40/E", Journal of General Virology, Feb. 1, 2008, pp. 359-368, vol. 89, No. 2.
Hitomi et al., "Human cytomegalovirus open reading frame UL11 encodes a highly polymorphic protein expressed on the infected cell surgace", Archives of Virology, Jul. 22, 1997, pp. 1407-1427, vol. 142, No. 7.
Garrigue et al., "Variability of UL18, UL40, UL111a, and US3 immunomodulatory genes among human cytomegalovirus clinical isolates from renal transplant recipients", Journal of Clinical Virology, Sep. 20, 2007, pp. 120-128, vol. 40, No. 2.
Baca Jones et al., "Rat cytomegalovirus infection depletes MHC II in bone marrow derived dendritic cells", Virology, May 25, 2009, pp. 78-90, vol. 388, No. 1.

* cited by examiner

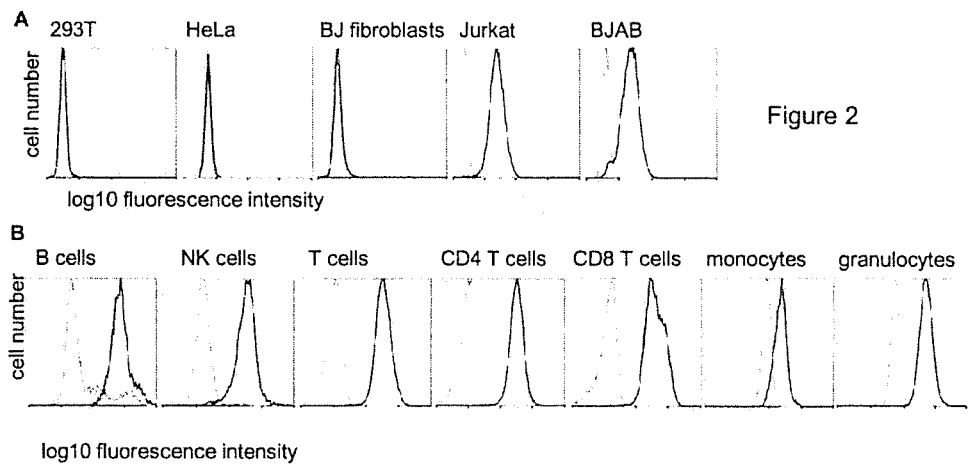
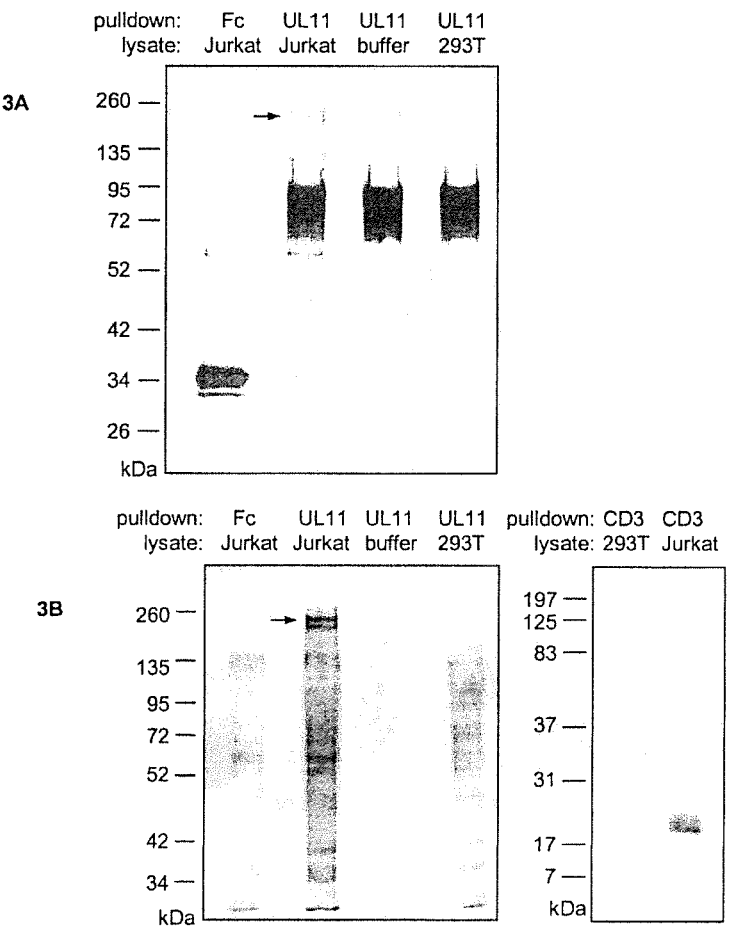
Figure 3

Fig. 5
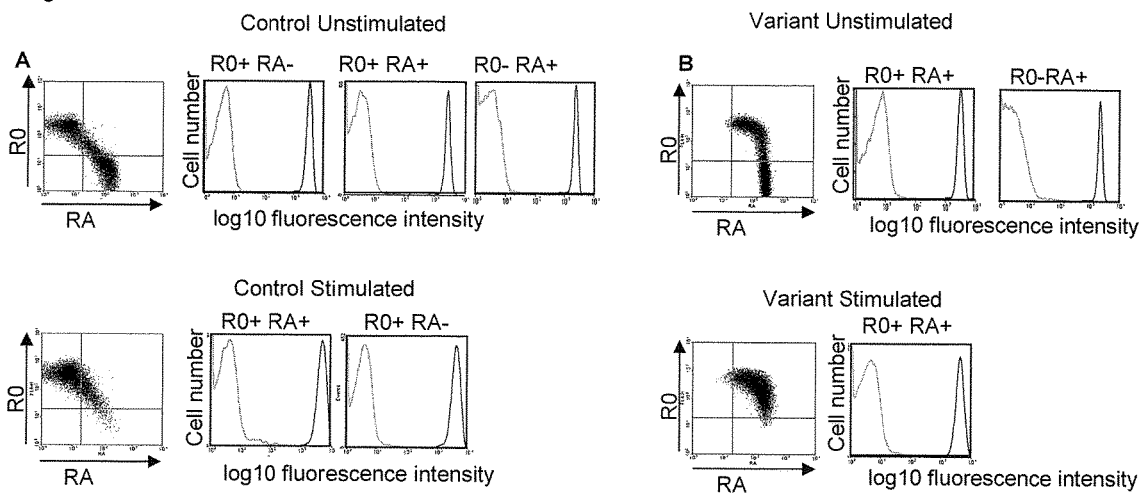
Fig. 6.
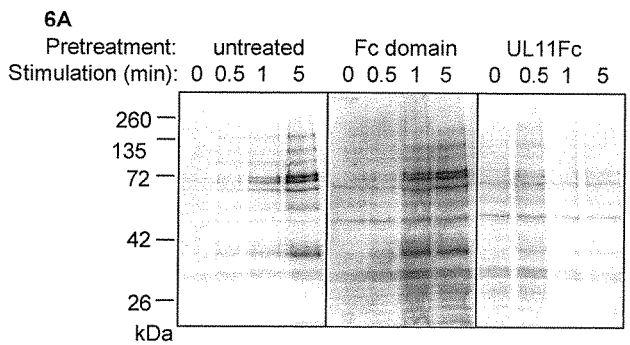
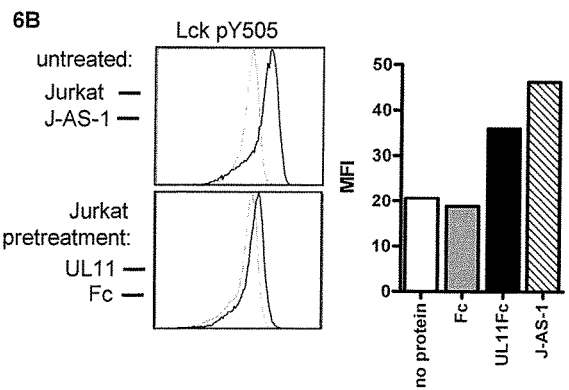
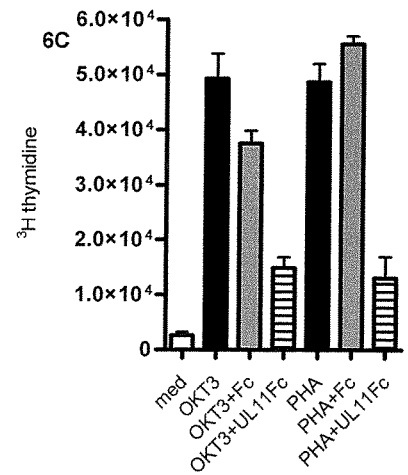

Fig. 9
A
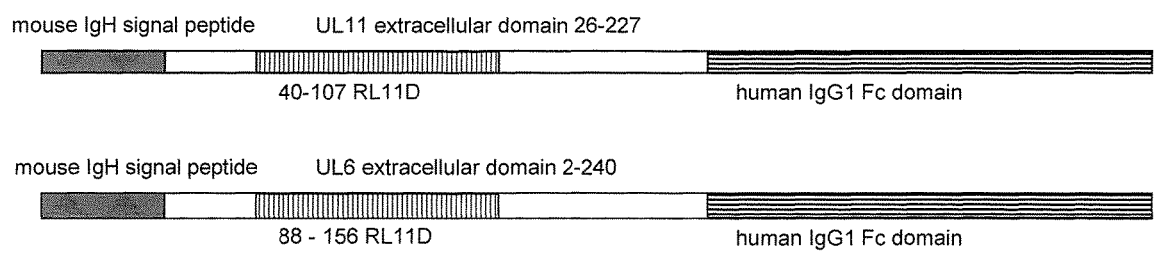
B
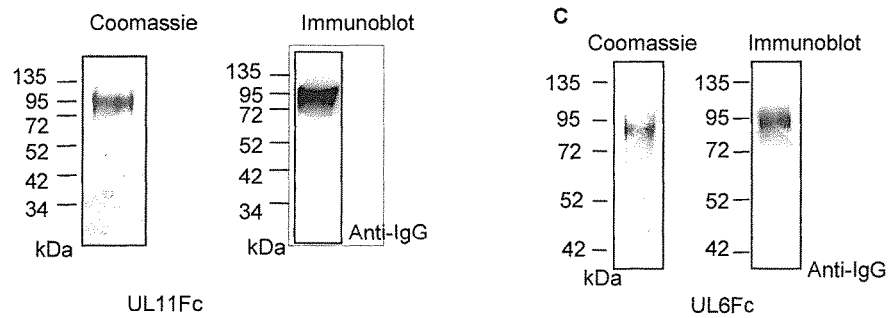
C
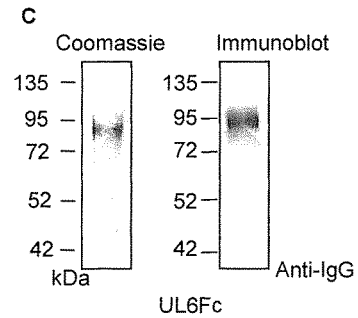
D
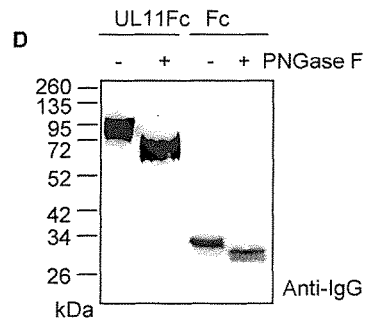

SEQUENCE LISTING

```
<160> NUMBER OF SEQ ID NOS: 22

<210> SEQ ID NO 1
<211> LENGTH: 819
<212> TYPE: DNA
<213> ORGANISM: Human cytomegalovirus
<220> FEATURE:
<221> NAME/KEY: CDS
<222> LOCATION: (1)..(816)

<400> SEQUENCE: 1
```

```
atg ctg ttc agg tac atc acc ttt cat cgc gaa aag gta ctt tac cta      48
Met Leu Phe Arg Tyr Ile Thr Phe His Arg Glu Lys Val Leu Tyr Leu
 1               5                  10                  15 acg gct gca tgc atc ttt ggt ggc tac atc agc ctc cac gat gcc tgc      96
Thr Ala Ala Cys Ile Phe Gly Gly Tyr Ile Ser Leu His Asp Ala Cys
                20                  25                  30 ata ccg gtg gtt ggc aaa ata ggt acc aac gtc acg ttg aac gcg gta     144
Ile Pro Val Val Gly Lys Ile Gly Thr Asn Val Thr Leu Asn Ala Val
         35                  40                  45 gat ttt cat ccc ggt gat cac gtt cgc tgg tct tac ggt ccc ggt ggg     192
Asp Phe His Pro Gly Asp His Val Arg Trp Ser Tyr Gly Pro Gly Gly
 50                  55                  60 gca ggc tac atg cta tgt gtt tac act ggt agt tgg aca gaa tac aaa     240
Ala Gly Tyr Met Leu Cys Val Tyr Thr Gly Ser Trp Thr Glu Tyr Lys
 65                  70                  75                  80 aag cca gac atc att ttt aag tgt tta tca aat aac agt ctt ctt tta     288
Lys Pro Asp Ile Ile Phe Lys Cys Leu Ser Asn Asn Ser Leu Leu Leu
                 85                  90                  95 att aac gta act gta aat tat acc aac act tac cgt acc ttg aca tcg     336
Ile Asn Val Thr Val Asn Tyr Thr Asn Thr Tyr Arg Thr Leu Thr Ser
            100                 105                 110 tta aac aat tgg gtt cac aat caa cat cac cat aaa ttt ccc gga tgg     384
Leu Asn Asn Trp Val His Asn Gln His His His Lys Phe Pro Gly Trp
        115                 120                 125 aac ttg gac aca tgt tac agt ctc aca gtg aac gaa aac ggt aca ttc     432
Asn Leu Asp Thr Cys Tyr Ser Leu Thr Val Asn Glu Asn Gly Thr Phe
    130                 135                 140 ccc act acc acc acc aaa aaa ccc act acg acc acg aga acg aca act     480
Pro Thr Thr Thr Thr Lys Lys Pro Thr Thr Thr Arg Thr Thr Thr
145                 150                 155                 160 acc acc aca aca aag aaa aca acc acg aga aca acc acc gcc gcc         528
Thr Thr Thr Thr Lys Lys Thr Thr Thr Thr Arg Thr Thr Thr Ala Ala
                165                 170                 175 aag aag acg acg ata agc act acc cat cat aaa cac tcc agt ccc aaa     576
Lys Lys Thr Thr Ile Ser Thr Thr His His Lys His Ser Ser Pro Lys
            180                 185                 190 aaa tcc agc acc cct aac agt cac gta gaa cat cac gtt ggt ttt gaa     624
Lys Ser Ser Thr Pro Asn Ser His Val Glu His His Val Gly Phe Glu
        195                 200                 205 gcc aca gca gcg gaa aca ccg tta caa cca agc cca cag cac caa cac     672
Ala Thr Ala Ala Glu Thr Pro Leu Gln Pro Ser Pro Gln His Gln His
    210                 215                 220 gtg gct aca cac gcc ctc tgg gtt tta gcg gtc gta atc gtt att atc     720
Val Ala Thr His Ala Leu Trp Val Leu Ala Val Val Ile Val Ile Ile
225                 230                 235                 240 atc att atc att ttc tac ttt cga ata ccg caa aag ctg tgg ctg ctc     768
Ile Ile Ile Ile Phe Tyr Phe Arg Ile Pro Gln Lys Leu Trp Leu Leu
                245                 250                 255 tgg cag cat gac aag cac ggc atc gtg ctc atc cct caa acc gat ctg     816
Trp Gln His Asp Lys His Gly Ile Val Leu Ile Pro Gln Thr Asp Leu
            260                 265                 270 tga                                                                 819

<210> SEQ ID NO 2
<211> LENGTH: 272
<212> TYPE: PRT
<213> ORGANISM: Human cytomegalovirus

<400> SEQUENCE: 2

Met Leu Phe Arg Tyr Ile Thr Phe His Arg Glu Lys Val Leu Tyr Leu
```

```
              1               5                  10                 15
         Thr Ala Ala Cys Ile Phe Gly Gly Tyr Ile Ser Leu His Asp Ala Cys
                          20                 25                 30

Ile Pro Val Val Gly Lys Ile Gly Thr Asn Val Thr Leu Asn Ala Val
                          35                 40                 45

Asp Phe His Pro Gly Asp His Val Arg Trp Ser Tyr Gly Pro Gly Gly
                          50                 55                 60

Ala Gly Tyr Met Leu Cys Val Tyr Thr Gly Ser Trp Thr Glu Tyr Lys
          65                 70                 75                 80

Lys Pro Asp Ile Ile Phe Lys Cys Leu Ser Asn Asn Ser Leu Leu Leu
                          85                 90                 95

Ile Asn Val Thr Val Asn Tyr Thr Asn Thr Tyr Arg Thr Leu Thr Ser
                         100                105                110

Leu Asn Asn Trp Val His Asn Gln His His His Lys Phe Pro Gly Trp
                         115                120                125

Asn Leu Asp Thr Cys Tyr Ser Leu Thr Val Asn Glu Asn Gly Thr Phe
                         130                135                140

Pro Thr Thr Thr Thr Lys Lys Pro Thr Thr Thr Arg Thr Thr Thr
         145                150                155                160

Thr Thr Thr Thr Lys Lys Thr Thr Thr Thr Arg Thr Thr Thr Ala Ala
                         165                170                175

Lys Lys Thr Thr Ile Ser Thr Thr His His Lys His Ser Ser Pro Lys
                         180                185                190

Lys Ser Ser Thr Pro Asn Ser His Val Glu His Val Gly Phe Glu
                         195                200                205

Ala Thr Ala Ala Glu Thr Pro Leu Gln Pro Ser Pro Gln His Gln His
                         210                215                220

Val Ala Thr His Ala Leu Trp Val Leu Ala Val Val Ile Val Ile Ile
         225                230                235                240

Ile Ile Ile Ile Phe Tyr Phe Arg Ile Pro Gln Lys Leu Trp Leu Leu
                         245                250                255

Trp Gln His Asp Lys His Gly Ile Val Leu Ile Pro Gln Thr Asp Leu
                         260                265                270

<210> SEQ ID NO 3
<211> LENGTH: 606
<212> TYPE: DNA
<213> ORGANISM: Human cytomegalovirus
<220> FEATURE:
<221> NAME/KEY: CDS
<222> LOCATION: (1)..(606)

<400> SEQUENCE: 3 atc agc ctc cac gat gcc tgc ata ccg gtg gtt ggc aaa ata ggt acc       48
Ile Ser Leu His Asp Ala Cys Ile Pro Val Val Gly Lys Ile Gly Thr
 1               5                  10                  15 aac gtc acg ttg aac gcg gta gat ttt cat ccc ggt gat cac gtt cgc       96
Asn Val Thr Leu Asn Ala Val Asp Phe His Pro Gly Asp His Val Arg
                 20                  25                  30 tgg tct tac ggt ccc ggt ggg gca ggc tac atg cta tgt gtt tac act      144
Trp Ser Tyr Gly Pro Gly Gly Ala Gly Tyr Met Leu Cys Val Tyr Thr
             35                  40                  45 ggt agt tgg aca gaa tac aaa aag cca gac atc att ttt aag tgt tta      192
Gly Ser Trp Thr Glu Tyr Lys Lys Pro Asp Ile Ile Phe Lys Cys Leu
         50                  55                  60 tca aat aac agt ctt ctt tta att aac gta act gta aat tat acc aac      240
Ser Asn Asn Ser Leu Leu Leu Ile Asn Val Thr Val Asn Tyr Thr Asn
 65                  70                  75                  80
```

```
                 65                  70                  75                  80
act tac cgt acc ttg aca tcg tta aac aat tgg gtt cac aat caa cat       288
Thr Tyr Arg Thr Leu Thr Ser Leu Asn Asn Trp Val His Asn Gln His
                 85                  90                  95 cac cat aaa ttt ccc gga tgg aac ttg gac aca tgt tac agt ctc aca       336
His His Lys Phe Pro Gly Trp Asn Leu Asp Thr Cys Tyr Ser Leu Thr
            100                 105                 110 gtg aac gaa aac ggt aca ttc ccc act acc acc acc aaa aaa ccc act       384
Val Asn Glu Asn Gly Thr Phe Pro Thr Thr Thr Thr Lys Lys Pro Thr
        115                 120                 125 acg acc acg aga acg aca act acc acc aca aca aag aaa aca acc acc       432
Thr Thr Thr Arg Thr Thr Thr Thr Thr Thr Thr Lys Lys Thr Thr Thr
    130                 135                 140 acg aga aca acc acc gcc gcc aag aag acg acg ata agc act acc cat       480
Thr Arg Thr Thr Thr Ala Ala Lys Lys Thr Thr Ile Ser Thr Thr His
145                 150                 155                 160 cat aaa cac tcc agt ccc aaa aaa tcc agc acc cct aac agt cac gta       528
His Lys His Ser Ser Pro Lys Lys Ser Ser Thr Pro Asn Ser His Val
                165                 170                 175 gaa cat cac gtt ggt ttt gaa gcc aca gca gcg gaa aca ccg tta caa       576
Glu His His Val Gly Phe Glu Ala Thr Ala Ala Glu Thr Pro Leu Gln
            180                 185                 190 cca agc cca cag cac caa cac gtg gct aca                               606
Pro Ser Pro Gln His Gln His Val Ala Thr
        195                 200

<210> SEQ ID NO 4
<211> LENGTH: 202
<212> TYPE: PRT
<213> ORGANISM: Human cytomegalovirus

<400> SEQUENCE: 4

Ile Ser Leu His Asp Ala Cys Ile Pro Val Val Gly Lys Ile Gly Thr
1               5                  10                  15

Asn Val Thr Leu Asn Ala Val Asp Phe His Pro Gly Asp His Val Arg
                20                  25                  30

Trp Ser Tyr Gly Pro Gly Gly Ala Gly Tyr Met Leu Cys Val Tyr Thr
            35                  40                  45

Gly Ser Trp Thr Glu Tyr Lys Lys Pro Asp Ile Ile Phe Lys Cys Leu
        50                  55                  60

Ser Asn Asn Ser Leu Leu Leu Ile Asn Val Thr Val Asn Tyr Thr Asn
65                  70                  75                  80

Thr Tyr Arg Thr Leu Thr Ser Leu Asn Asn Trp Val His Asn Gln His
                85                  90                  95

His His Lys Phe Pro Gly Trp Asn Leu Asp Thr Cys Tyr Ser Leu Thr
            100                 105                 110

Val Asn Glu Asn Gly Thr Phe Pro Thr Thr Thr Thr Lys Lys Pro Thr
        115                 120                 125

Thr Thr Thr Arg Thr Thr Thr Thr Thr Thr Thr Lys Lys Thr Thr Thr
    130                 135                 140

Thr Arg Thr Thr Thr Ala Ala Lys Lys Thr Thr Ile Ser Thr Thr His
145                 150                 155                 160

His Lys His Ser Ser Pro Lys Lys Ser Ser Thr Pro Asn Ser His Val
                165                 170                 175

Glu His His Val Gly Phe Glu Ala Thr Ala Ala Glu Thr Pro Leu Gln
            180                 185                 190

Pro Ser Pro Gln His Gln His Val Ala Thr
        195                 200
```

<210> SEQ ID NO 5
<211> LENGTH: 14
<212> TYPE: PRT
<213> ORGANISM: artificial
<220> FEATURE:
<223> OTHER INFORMATION: synthetic peptide

<400> SEQUENCE: 5

Gly Lys Pro Ile Pro Asn Pro Leu Leu Gly Leu Asp Ser Thr
1               5                   10

<210> SEQ ID NO 6
<211> LENGTH: 30
<212> TYPE: DNA
<213> ORGANISM: artificial
<220> FEATURE:
<223> OTHER INFORMATION: synthetic oligonucleotide

<400> SEQUENCE: 6
agtcggatcc aattacctgt ggtagaatgc                              30

<210> SEQ ID NO 7
<211> LENGTH: 30
<212> TYPE: DNA
<213> ORGANISM: artificial
<220> FEATURE:
<223> OTHER INFORMATION: synthetic oligonucleotide

<400> SEQUENCE: 7
ggccggatcc ttacgtagaa tcaagaccta                              30

<210> SEQ ID NO 8
<211> LENGTH: 56
<212> TYPE: DNA
<213> ORGANISM: artificial
<220> FEATURE:
<223> OTHER INFORMATION: synthetic oligonucleotide

<400> SEQUENCE: 8
aagacaccgg gaccgatcca gcctggatcc gccaccatgc tgttcaggta catcac      56

<210> SEQ ID NO 9
<211> LENGTH: 50
<212> TYPE: DNA
<213> ORGANISM: artificial
<220> FEATURE:
<223> OTHER INFORMATION: synthetic oligonucleotide

<400> SEQUENCE: 9
tatagagtat acaatagtga cgtgggatcc tcacttgtac agctcatcca            50

<210> SEQ ID NO 10
<211> LENGTH: 72
<212> TYPE: DNA
<213> ORGANISM: artificial
<220> FEATURE:
<223> OTHER INFORMATION: synthetic oligonucleotide

<400> SEQUENCE: 10
aaccgtcaga tcgcctggag acgccatcca cgctgttttg acctccatag aagacaccgg   60
gaccgatcca gc                                                     72

<210> SEQ ID NO 11

<211> LENGTH: 74
<212> TYPE: DNA
<213> ORGANISM: artificial
<220> FEATURE:
<223> OTHER INFORMATION: synthetic oligonucleotide

<400> SEQUENCE: 11
ggcgtgacac gtttattgag taggattaca gagtataaca tagagtataa tatagagtat    60
acaatagtga cgtg    74

<210> SEQ ID NO 12
<211> LENGTH: 45
<212> TYPE: DNA
<213> ORGANISM: artificial
<220> FEATURE:
<223> OTHER INFORMATION: synthetic oligonucleotide

<400> SEQUENCE: 12
aagacaccgg gaccgatcca gcctggatcc gccctctcc ctccc    45

<210> SEQ ID NO 13
<211> LENGTH: 28
<212> TYPE: DNA
<213> ORGANISM: artificial
<220> FEATURE:
<223> OTHER INFORMATION: synthetic oligonucleotide

<400> SEQUENCE: 13
cgggatccat cagcctccac gatgcctg    28

<210> SEQ ID NO 14
<211> LENGTH: 28
<212> TYPE: DNA
<213> ORGANISM: artificial
<220> FEATURE:
<223> OTHER INFORMATION: synthetic oligonucleotide

<400> SEQUENCE: 14
ccggtcgact gtagccacgt gttggtgc    28

<210> SEQ ID NO 15
<211> LENGTH: 31
<212> TYPE: DNA
<213> ORGANISM: artificial
<220> FEATURE:
<223> OTHER INFORMATION: synthetic oligonucleotide

<400> SEQUENCE: 15
cggcggccgc gccaccatga acttcgggtt c    31

<210> SEQ ID NO 16
<211> LENGTH: 28
<212> TYPE: DNA
<213> ORGANISM: artificial
<220> FEATURE:
<223> OTHER INFORMATION: synthetic oligonucleotide

<400> SEQUENCE: 16
cggaattctc atttacccgg agacaggg    28

<210> SEQ ID NO 17
<211> LENGTH: 31
<212> TYPE: DNA
<213> ORGANISM: artificial
<220> FEATURE:
<223> OTHER INFORMATION: synthetic oligonucleotide

```
<400> SEQUENCE: 17
cggcggccgc gccaccatga acttcgggtt c                                    31

<210> SEQ ID NO 18
<211> LENGTH: 28
<212> TYPE: DNA
<213> ORGANISM: artificial
<220> FEATURE:
<223> OTHER INFORMATION: synthetic oligonucleotide

<400> SEQUENCE: 18
cggaattctc atttacccgg agacaggg                                        28

<210> SEQ ID NO 19
<211> LENGTH: 29
<212> TYPE: DNA
<213> ORGANISM: artificial
<220> FEATURE:
<223> OTHER INFORMATION: synthetic oligonucleotide

<400> SEQUENCE: 19
cgggatccca tgctaagata aacgggtgg                                       29

<210> SEQ ID NO 20
<211> LENGTH: 31
<212> TYPE: DNA
<213> ORGANISM: artificial
<220> FEATURE:
<223> OTHER INFORMATION: synthetic oligonucleotide

<400> SEQUENCE: 20
ccggtcgacg aatgccaagt tagttatgtt c                                    31

<210> SEQ ID NO 21
<211> LENGTH: 51
<212> TYPE: DNA
<213> ORGANISM: artificial
<220> FEATURE:
<223> OTHER INFORMATION: synthetic oligonucleotide

<400> SEQUENCE: 21
aagacaccgg gaccgatcca gcctggatcc gccaccatga acttcgggtt c              51

<210> SEQ ID NO 22
<211> LENGTH: 54
<212> TYPE: DNA
<213> ORGANISM: artificial
<220> FEATURE:
<223> OTHER INFORMATION: synthetic oligonucleotide

<400> SEQUENCE: 22
tatagagtat acaatagtga cgtgggatcc tcatttaccc ggagacaggg agag           54
```

IMMUNE SUPPRESSOR AND ITS USE

The present invention relates to a new binder molecule useful e.g. as an immune suppressor. In particular, it has been recognized that the UL11 protein of human cytomegalovirus binds to the CD45 molecule, potentially altering the immune system of an individual. In addition, the present invention relates to binder molecules, in particular, fusion molecules, containing the CD45 binding domain of the UL11 protein in combination with a molecule of interest for delivery of said molecule to cells expressing the CD45 molecule. Moreover, the present invention relates to pharmaceutical compositions comprising the UL11 protein of human cytomegalovirus, or derivatives or analogs thereof, or a nucleic acid sequence encoding the same.

PRIOR ART

The herpesviridae are a large family of DNA viruses that causes diseases in animals, in humans. The members of this family are also known as herpes viruses. There are 8 human herpesviruses and the order Herpesvirales contains 90 species in all, classified into 3 families, 3 subfamilies and 17 genera.

All herpes viruses are nuclear replicating, examples of herpesviridae include herpes simplex virus, Varicella zoster virus, Epstein-Barr virus, Cytomegalovirus (CMV) but also roseolovirus. For example, the human herpes virus 1 and 2 are species of the simplexvirus genus while the human herpes virus 5 is a species of the cytomegalovirus genus.

The human cytomegalovirus (HCMV) contains over 200 predicted open reading frames in the 230 kb genome which consists of long and short unique sequences (UL and US) flanked by inverted repeats. A number of said ORFs can encode glycoproteins that have characteristic signal sequences, transmembrane regions and potential N-linked glycolysation sites. Infection of immuno competent individuals with human cytomegalovirus rarely results in symptomatic disease. However, following primary infection children and even adults often shed the virus in saliva or urine for weeks or months suggesting that the immune system has to expend a lot of effort for clearing the CMV infection. Cellular immunity, in particular natural killer cells (NK cells) and CD8+ T cells, has been found to be pivotal in controlling CMV. Though the induction of a strong cellular immune response and of neutralising antibodies occurs, CMV is able to establish a latent infection, and reactivation as well as reinfection with multiple CMV strains seems to be quite frequent. These properties of CMV have been ascribed to the expression of a series of viral immunomodulatory proteins. In individuals with weakened or immature immune system, the delicate balance between host immune control and viral immunmodulation can easily be shifted in favour of the virus, resulting in viremia and end organ disease associated with morbidity and even mortality in CMV-infected transplant recipients, AIDS patients or children congenitally infected with CMV. It is a long standing observation that T lymphocytes in patients with acute CMV infection display reduced proliferation capacity that may result in transient immunosuppression associated with the risk for secondary infection. A number of mechanisms of CMV have been proposed that may interfere with the priming of T cells as well as with their function in the effector phase. Well established is the inhibition of MHC class I antigen presentation pathways by CMV, limiting the recognition and lysis of infected cells by cytolytic T lymphocytes. Further, it is described that the secretion of host and virally encoded suppressive factors from CMV-infected cells acts on the ability of T cells to proliferate, that is, the virus induces enhanced TGF-β and soluble CD83 secretion and itself encodes an Il-10 homologue that suppresses T cell proliferation. Other suppressive functions require direct contact between infected cells and T cells. An example is the upregulation of pro-apoptotic ligands on the surface of CMV infected dendritic cells that can induce apoptosis in activated T cells. The observation that T cells, which were in contact with CMV-infected cells, are unable to proliferate normally, implies the existence of additional suppressive mechanisms. One possibility could be the interaction of CMV-encoded surface proteins with regulatory or inhibitory receptors on T cells. Cellular proteins and also immunomodulatory proteins of various viruses that mediate the interaction with surface proteins of immune cells often contain immunoglobulin-like or MHC-like domains.

The CMV genome encodes a number of putative transmembrane proteins with such a property, the most prominent being the RL11 family that includes 14 largely uncharacterised proteins. The defining motif of this family is the RL11 domain, which has a limited sequence homology to immunoglobulin domains and to the immunomodulatory E3 proteins of adenoviruses, indicating a potential for the RL11 proteins to interact with components of the immune system. The RL11 protein encodes an Fc-receptor binding human immunoglobulins and mediates escape from recognition by anti-viral immunoglobulins. RL11 protein is the only member to be functionally characterised so far of the RL11 family.

Immunosuppression is a relevant tool in various applications. For example, immunosuppression is relevant in transplantation but also other type of diseases, disorders or conditions. For example, immunesuppression is relevant in the field of inflammation, autoimmune diseases and other diseases, disorders or conditions associated with unusual activation of immune competent cells, like activation of T lymphocytes or hyperproliferation or abnormal proliferation of T lymphocytes but also B lymphocytes and other mononuclear cells, e.g. as it is the case in hematopoietic malignancies.

A typical approach in the treatment of diseases involving the downregulation of immune responses includes the elimination or inactivation of pathogenic leucocytes and the potential induction of tolerance to inactivate pathological immune responses.

For example, organ, cell and tissue transplant rejection and the various autoimmune diseases are primarily the result of T cell mediated immune response triggered by T cells.

For example, restricted proliferative capacity of T cells from HCMV infected patients has been linked with defects in T cell receptor signalling.

For preventing or treating immune system diseases, disorders or conditions, like the conditions identified above, the need for effective immune suppressors is obvious.

At the present, immune suppressors used in organ or tissue transplantation comprise monoclonal antibodies against cytokine receptors, e.g. anti IL2 receptor antibodies or inhibitors of calcineurin e.g. the substance tacrolimus. Other approaches for immune suppression involves the inhibition of the mTor-signalling pathway, e.g. by administering substances like everolimus or sirolimus. Furthermore, the immune suppression is affected by combinatorial therapy using DNA synthesis inhibitors like mycophenolate and azathioprin as well as long term therapy with corticosteroids.

Since at least 70000 organ transplantations occur per year world wide there is a need for effective immune suppressors. Beside transplantation, the prophylaxis and treatment of autoimmune diseases but also of hematopoietic malignancies represent important areas of interest where the need for effective immune suppressors is evident.

The present invention aims in providing effective immune suppressors based on binding of suitable molecules to the CD45 protein present on mononuclear cells involved in the immune response.

BRIEF DESCRIPTION OF THE PRESENT INVENTION

In a first aspect, the present invention provides a composition useful as an immune suppressor comprising a polypeptide of the extracellular domain of the UL11 protein of cytomegalovirus, derivatives or homologs thereof, or a nucleic acid sequence encoding the same. That is, the present inventors recognized that the CMV UL11 protein interacts with the CD45 receptor phosphatase on the surface of T cells, thus, inhibiting downstream signalling steps and restricting T cell proliferation.

It is preferred that the UL11 protein or polypeptide, derivatives or homologs thereof, or the nucleic acid sequence encoding the same is derived from the cytomegalovirus, in particular, the human cytomegalovirus protein.

In another aspect, the present invention relates to a binding molecule, preferably, a fusion polypeptide, comprising as a binding component at least the extracellular domain of the UL11 protein of cytomegalovirus, derivatives or homologs thereof. In particular, the fusion protein having binding capacity to CD45 is a fusion protein containing the UL11 protein and a molecule of interest.

Further, the present invention relates to pharmaceutical compositions comprising the extracellular domain of the UL11 protein of cytomegalovirus, derivatives or homologs thereof, or a nucleic acid sequence encoding the same. Said pharmaceutical composition is particularly useful for the prophylaxis and/or treatment of immune system disorders and inflammation.

Finally, the present invention relates to a method for designing of immune-suppressive molecules.

BRIEF DESCRIPTION OF THE DRAWINGS

FIG. 2. UL11 interacts with leukocytes. A) Purified UL11Fc, or the Fc domain were incubated with cell lines and interactions detected by FACS, using PE-conjugated anti-IgG for detection. Black lines depict UL11Fc binding and grey lines Fc binding. B) Purified UL11Fc or Fc proteins were incubated with primary PBMCs. Surface markers and cell size were used to set gates for different leukocyte subpopulations. Interactions were detected and depicted as in B).

FIG. 3. UL11 interacts with a glycoprotein on the surface of T cells, with an approximate size of 200 kDa. A) Lysates of Jurkat or 293T cells, or lysis buffer, were incubated with UL11Fc or the Fc domain and protein A sepharose beads. The bound proteins were detected by silver staining of a SDS-PAGE gel. B) Jurkat or 293T cells were incubated with membrane impermeable biotin prior to lysis. Proteins interacting with UL11Fc, the Fc domain or anti-CD3E were precipitated as in B) and detected after blotting by using HRP-streptavidin. A doublet at approx. 200 kDa is indicated.

FIG. 5. UL11 interacts with cells expressing both long and short isoforms of CD45. Primary T cells from donors with control (A) or variant (B) CD45 were stimulated with mitogen or untreated. UL11Fc or the Fc domain was incubated with these cells in the presence of anti-CD45RA or anti-CD45R0 antibodies. Subsequent detection of UL11Fc and the Fc domain was with PE-labelled anti-IgG. Cells were gated as R0 positive, RA positive, or R0 and RA positive using the indicated quadrants. The interactions of UL11Fc with the three subsets are shown in black, those of the Fc domain are shown in grey.

FIG. 6. UL11 treatment results in increased inactive Lck and reduced tryrosine phosphorylation upon stimulation through the TCR and inhibits T cell proliferation. A) Tyrosine phosphorylation in Jurkat cell lysates was detected using an anti-phosphotyrosine antibody after blotting. Jurkat cells were stimulated with cross-linked anti-CD3 antibody for the indicated times prior to lysis or pretreated with UL11Fc or the Fc domain (2.5 µg) for 30 min before stimulation. B) Levels of pY505 lck were measured by intracellular FACS staining using anti-pY505 and a PE-labelled secondary antibody. pY505 lck in J-AS-1 CD45 deficient Jurkat cells was compared with wild type Jurkat cells (upper panel; J-AS-1 are shown in black, Jurkat in grey). pY505 was measured in Jurkat cells after pre-treatment with UL11Fc or the Fc domain (lower panel; UL11Fc treated cells are shown in black, Fc treated cells in grey). Mean Fluoresence Intensities (MFI) are shown from one representative experiment of three. C) Primary T cells were incubated in plates coated with anti-CD3 or with phytohaemagglutinin (PHA), with BSA, UL11Fc or the Fc domain (2 µg) for 3 days. Following incubation for 16 h with 3H thymidine, radionucleotide incorporation was measured. All samples were handled in triplicate. Representative data from one of three experiments are shown.

FIG. 9 The predicted extracellular domains of UL11 and UL6 were purified as Fc fusion proteins. Cartoons of predicted extracellular domains as Fc fusion proteins (A). UL11Fc (B) and UL6Fc (C) were harvested from supernatants, and purified using protein A sepharose. The purified proteins were detectable by Coomassie blue staining of SDS-PAGE gels or by immunoblotting using HRP conjugated anti-IgG for detection. D) UL11Fc or the control Fc domain were treated with PNGase F. Proteins were detected after immunoblotting as in C)

DETAILED DESCRIPTION OF THE PRESENT INVENTION

Figure 1:
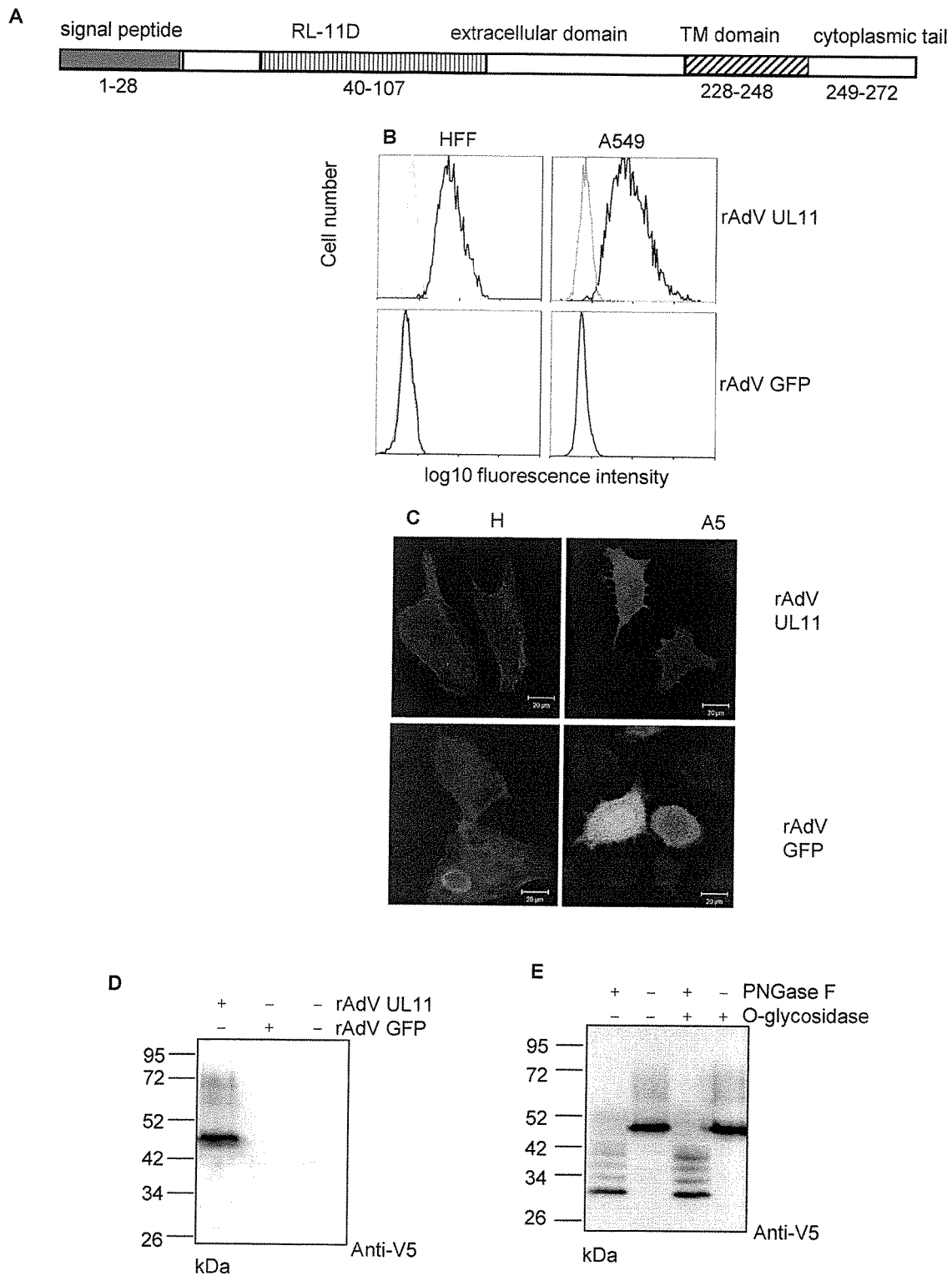
FIG. 1. UL11 is a surface expressed glycoprotein. A) Cartoon of predicted UL11 domain structure, based on predictions using TMHMM Server v.2.0 and SO-SUIsignal. B) HFF or A549 cells were transduced using recombinant adenoviruses expressing UL11 and GFP (rAdV UL11) or GFP alone (rAdV GFP). Detection of surface expressed UL11 by FACS was performed using anti-UL11 rabbit antiserum and PE-coupled anti-rabbit antibodies. Black lines show detection using anti-UL11 antiserum and grey lines show pre-immune serum. C) HFF and A549 cells were transduced as in B) and surface expressed UL11 visualised by confocal microscopy, using anti-UL11 antiserum and Alexa-568 labelled anti-rabbit antibodies for detection. The size bar indicates 20 µm. D) Lysates of rAdV UL11, rAdV GFP or mock transduced A549 cells were immunoblotted using a mouse anti-V5 antibody and HRP-conjugated anti-mouse secondary antibody for detection. E) rAdV UL11 transduced A549 cell lysates were treated with peptide N-glycosidase F (PNGase F), endo-α-N-acetylgalactosaminidase (O-glycosidase) or mock treated as indicated. After blotting, proteins were detected as in D).

In a first aspect, the present invention provides new binding molecules of CD45, e.g. inhibitors of CD45 mediated signalling useful as immune suppressors. In particular, the present invention provides binding molecules of the CD45 molecule, e.g. useful as immune suppressors comprising the extracellular domain of the UL11 protein of cytomegalovirus, derivatives or homologs thereof, or a nucleic acid sequence encoding the same.

Derivatives and homologs may be full length or other than full length. Derivatives or homologs of the nucleic acids or proteins of the invention include, but are not limited to, molecules comprising regions that are substantially homologous to the nucleic acids or proteins of the invention, in various embodiments, by at least about 50%, 60%, 70%, 80%, or 95% identity (with a preferred identity of 80-95% or more) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins under stringent, moderately stringent, or low stringent conditions. See e.g. Ausubel, et al, CURRENT PROTOCOLS IN MOLECULAR BIOLOGY, John Wiley & Sons, New York, N.Y., 1993, and below.

That is, homologous peptides or polynucleotides (homologs) of the invention have at least about 50% sequence identity, generally at least about 60% sequence identity, and can have at least about 70% sequence identity or 80% sequence identity or more as compared to a reference peptide of Seq. ID. No. 2 or 4 or polynucleotide of Seq. ID No. 1 or 3, respectively.

For purposes of determining sequence identity, conservative amino acid substitutions such as a substitution of amino acids that have a aliphatic hydrophobic side chain (e.g., alanine, leucine, isoleucine, valine), or of amino acids that have an acid side chain (e.g., aspartic acid, glutamic acid), or of amino acids that have a basic side chain (arginine, lysine), or the like, are considered to be identical. In addition, a determination of homology can allow for one or a few insertions or deletions, preferably one or two insertions or deletions, provided that such insertions or deletions are counted as an amino acid that is not identical for purposes of the comparison. As such, homologous peptides can differ in length by one, two, or a few amino acids, provided the minimum amount of sequence identity is maintained.

It is preferred that the composition for use as a immune suppressor according to the present invention comprises a UL11 polypeptide, derivative or homolog, or a nucleic acid sequence encoding the same. In a preferred embodiment, the UL11 polypeptide is a soluble molecule, e.g. a soluble polypeptide not containing the transmembrane region of the UL11 protein.

It is particularly preferred that the UL11 polypeptide or the nucleic acid sequence encoding the same is derived from cytomegalovirus, in particular, the human cytomegalovirus.

In this connection, the term "polypeptide" as used herein is intended to encompass a singular "polypeptide" as well as plural "polypeptides" and comprises any chain or chains of two or more amino acids. Thus, as used herein, said term includes oligopeptides of two to fifty amino acids length as well as polypeptides having at least 51 amino acids. The term further includes polypeptides which have undergone posttranslational modifications, for example, glycosylation, acetylation, phosphorylation, amidation, derivatisation by known protecting/blocking groups, protolytic cleavage or modification by non-naturally occurring amino acids.

Furthermore, the term nucleic acid or nucleic acid fragment refers to any one or more nucleic acid segments, e.g. DNA or RNA fragment present in a polynucleotide. The term "polynucleotide" or "nucleic acid sequence" is intended to encompass a singular nucleic acid or nucleic acid fragment as well as plural nucleic acids or nucleic acid fragments. In certain embodiments, the polynucleotide, nucleic acid sequence, nucleic acid or nucleic acid fragment is a DNA.

The terms "polypeptide or protein" and "nucleic acid sequence" include also parts or fragments of said polypeptide or protein and nucleic acid sequence as long as said polypeptides, proteins as well as nucleic acid sequences encoding the same bind or interact with CD45.

It is preferred that the UL11 protein or polypeptide are UL11 HCMV including all variants from the different strains of the virus.

As demonstrated, the human cytomegalovirus UL11 polypeptide is able to bind to the CD45 receptor molecule and, in addition, allows to inhibit downstream signalling steps, thus, restricting T cell proliferation.

UL11 is predicted to be a type I transmembrane protein and has previously reported to be expressed on surface of HEL fibroblasts infected with the highly passaged AD169 laboratory strain of HCMV.

The CD45 protein is an essential regulator of the TCR signalling pathway, yet, it can enhance as well as inhibit signal transduction. The absence of CD45 leads to a SCID phenotype in humans and mice. The key substrate of the CD45 phosphatase in TCR signalling is the src family kinase (SFK) Lck, which is in close proximity to the TCR and provides the essential first step for the transfer of an incoming stimulatory signal to downstream effector molecules by phosphorylation of immunoreceptor tyrosine-based activation motives (ITAMs) in subunits of the T cell complex. As indicated, CD45 may have activation but also inhibitory functions depending on the downstream process. CD45 is the only phosphatase known so far to dephosphorylate the inhibitory tyrosine of Lck, and the action of CD45 is therefore essential in setting the threshold at which incoming stimulation signals can be transduced into effects.

So far, lectins, such as galectin-1 are described to interact with the oligosaccharide moieties on the extracellular domains of CD45 and can regulate the activity, but no specific ligand binding solely to CD45 has been identified. In the art, therapeutic humanised antibodies against CD45 isoforms are described. EP 1 664 122 relates to such humanised antibodies binding to CD45. Furthermore, WO 02/072832 A2 relates to therapeutic binding molecules allowing binding to CD45 isoforms.

CD45 is described as a critical regulator of signalling thresholds in immune cells, see e.g. Hermiston, M. L., et al., Annu. Ref. Immunol. 2003, 21, 107-37. It is described that CD45 glycosylation shall control T cell life and death as discussed by Earl L. A. and Baum L. G., Immunology and cell biology, 2008, 86, 608-615.

Due to alternative splicing, five dominant CD45 isoforms have been described, namely, CD45R0, RA, RB, RBC, and RABC. These isoforms are differentially expressed throughout lymphoid cell development and differentiation. For example, the dominant CD45 isoform for most stages of T cell development is CD45RB whereas for B cells, the dominant form is CD45RABC. In contrast, memory cells of both B and T cell lineages express lower molecular weight isoforms of CD45, like CD45R0. In addition, CD45 expression is described on other mononuclear cells like NK cells, monocytes and neutrophils. The binding molecules for CD45 described so far typically differentiate between the CD45 isoforms, a binding molecule other than antibodies allowing detection and/or binding of all CD45 isoforms by binding to an extracellular domain of CD45 has not been described so far.

It has now been recognized that the UL11 protein is a binding molecule of all isoforms of CD45 including CD45RA, CD45RB, CD45RBC, CD45RABC and CD45R0. Thus, it is possible to provide a binding molecule binding to all CD45 isoforms.

In a preferred embodiment of the present invention, the binding molecule is useful as an immune suppressor. In another preferred embodiment, the binding molecule is a molecule which may not act as an inhibitor but as a binder molecule only. For example, the binding molecule may act as an anti-viral agent. Said binder molecule is preferably a fusion molecule comprising the binding element of the UL11 protein of cytomegalovirus, derivatives or homologs thereof, in combination with a molecule of interest. Thus, said fusion molecule allows to deliver the molecule of interest fused to the UL11 protein domain to cells expressing CD45.

It is particularly preferred that the binding molecule comprises at least the extracellular domain of the UL11 polypeptide of the cytomegalovirus, in particular, the human cytomegalovirus.

The binding molecule may also be in form of a nucleic acid sequence encoding the fusion molecule comprising at least the extracellular domain of the UL11 protein of cytomegalovirus, derivatives or homologs thereof, in combination with a molecule of interest to be delivered to cells expressing CD45.

It is preferred that the herpesvirus is a CMV, in particular, a HCMV.

Alternatively, the molecule of interest may be an active ingredient, e.g. a pharmaceutical, a label, a marker, a drug or prodrug, a radioactive component, a cytotoxic or apoptosis inducing component, a cell-proliferation-inducing component, a cell-activation-inducing component or a cell-differentiation inducing component.

That is, the molecule of interest may be an active component or may be a marker or label. The skilled person is well aware of suitable marker or label molecules. In addition, the skilled person is well aware of fusing or linking the UL11 polypeptide or the nucleic acid sequence encoding the same with the second molecule of interest. It is preferred, that the binding molecule is an inhibitor of CD45 signalling, thus, eventually having immune suppressor activity. That is, the present invention provides an immune suppressor comprising the extracellular domain of the UL11 protein of cytomegalovirus, derivatives or homologs thereof, or a nucleic acid sequence encoding the same.

The term extracellular domain of the UL11 protein of cytomegalovirus, derivatives or homologs thereof, or a nucleic acid sequence encoding the same include peptides of the amino sequence of Seq. ID No. 2 or 4 or a peptide that is functioning the same as the protein comprising the amino sequence of Seq. ID No. 2 or 4, being composed of the amino acid sequence modified by substitution, deletion, insertion and/or addition of one or more amino acid sequence.

That is, the term "UL11 protein" or "UL11 polypeptide" comprises derivatives or homologs containing mutations having the functionality of binding to CD45, in particular, of binding and having immune suppressor activity by reducing T cell proliferation or inhibiting downstream signalling as shown herein. In addition, said term include variants of different CMV, in particular, HCMV strains.

The nucleic acid sequence encoding said UL11 polypeptide is preferably a DNA sequence comprising the coding region of the nucleic acid sequence of Seq. ID No. 1 or 3 or nucleic acid sequence derivates encoding for the peptide of the same amino acid sequence but having a different nucleic acid sequence due the genetic code degeneration.

As identified above, it is preferred that the binding molecule is an inhibitor of the CD45 signalling, in particular, an immune suppressor. That is, another embodiment of the present invention relates to a pharmaceutical composition comprising the UL11 peptide or the nucleic acid sequence encoding the same. Said pharmaceutical composition is particularly useful for the prophylaxis and/or treatment of immune system disorders and inflammation. A typical example of an immune disease disorder is cell, tissue or organ transplant rejection. The immune suppressor of the present invention is particularly useful for inhibiting a transplant rejection. The immune suppressor may be used prior to transplantation and/or concurrently, and/or following transplantation of the cell, tissue or organ. In another aspect, the pharmaceutical composition is particularly useful in anti-inflammatory treatment as well as for the treatment of autoimmune diseases or other immune system disorders. Typical examples of autoimmune diseases includes inflammatory bowel disease, multiple sclerosis, type 1 diabetes, systemic erythematosus or rheumatoid arthritis but also hematopoietic malignancies, including leukaemias, lymphomas and myelomas.

The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, patches and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin (18th ed., Mack Publishing Co., Easton, Pa. (1990)). Such compositions will contain a therapeutically effective amount of the aforementioned immune suppressor, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury and/or decreased tumor growth and/or tumor volume decrease, and/or tumor necrosis, and/or tumor apoptosis.

In vitro assays may optionally be employed to help identifying optimal dosage ranges. The precise dose to be employed in the formulation will also depend on the route of administration, and the seriousness of the disease or disorder, and should be decided according to the judgement of the practitioner and each patient's circumstances. Effective doses may be extrapolated from dose-response curves derived from in vitro or animal model test systems. Preferably, the pharmaceutical composition is administered directly or in combination with an adjuvant. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In the context of the present invention the term "subject" means an individual in need of a therapy that can be alleviated or cured by administering the immune suppressor according to the present invention to the individual. Preferably, the subject is a vertebrate, even more preferred a mammal, particularly preferred a human.

The term "administered" means administration of a therapeutically effective dose of the aforementioned pharmaceutical composition comprising the immune suppressor or binding molecule comprising the molecule of interest to an individual.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intra-arterial, intranodal, intramedullary, intrathecal, intraventricular, intranasally, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 μg; however, doses below or above this exemplary range are envisioned, especially considering the aforementioned factors.

That is, the present invention allows the treatment of individuals suffering from immune system disorders and inflammation. For example, the individual are treated for inhibiting transplant rejection or for preventing or treating autoimmune diseases and other inflammatory diseases or hematopoietic malignancies as identified herein.

In another aspect, the present invention provides a method for identifying CD45 binding molecules, like immunosuppressive molecules comprising the step of designing CD45 receptor binder molecules based on the extracellular domain of the UL11 polypeptide. Further, it is possible to screen for immunosuppressive molecules using the UL11 peptide as a reference molecule, e.g. for competitive binding to CD45 etc. The skilled person is well aware of suitable methods for screening procedures. That is, in another aspect, the present invention relates to a method for designing of immunosuppressive molecules comprising the step of
  a) molecular modelling of candidate molecules based on the UL11 protein of cytomegalovirus or derivatives or homologs thereof,
  b) testing said candidate molecules of step a) on their ability to bind to CD45, optionally testing said molecules identified in step b) as CD45 binding molecules on their ability to suppress activity and/or proliferation and/or inducing apoptosis or cell death in hematopoietic cells, in particular, B- or T-cells.

The invention will be described further by reference to examples without being limited thereon.

Examples

Material and Methods
Cell Culture and Viruses

A549 lung adenocarcinoma epithelial cells and human foreskin fibroblasts (HFF) were maintained in DMEM (Biochrom, Berlin, Germany) containing 10% FCS, 2 mM glutamine and 1% non-essential amino acids. 293T and 293A cells were maintained in DMEM (Biochrom) containing 10% FCS. Jurkat T cells were cultured in RPMI 1640 (Biochrom) with 2 mM glutamine and 10% FCS. J(AS)-1 cells, kindly provided by D. Rothstein, University of Pittsburgh, USA, were cultured in RPMI 1640 (Biochrom) with 4 mM glutamine, 20 mM Hepes, 10% FCS and G418 (0.5 mg/ml). HPB.45.0 cells, a CD45-negative variant of the HPB-ALL leukaemic T-cell line, kindly provided by B. Schraven (University of Magdeburg, Germany) were maintained in RPMI 1640 (Biochrom) with 4 mM glutamine, 20 mM Hepes and 10% FCS. For protein production, retinal pigment epithelium (RPE) or 293T cells were maintained in serum free Pro293a-CDM (Lonza, Cologne, Germany), containing 2 mM glutamine.

PBMCs were flushed from leukocyte filters used to prepare erythrocytes from healthy voluntary blood donors for transfusion, obtained from the Institute of Transfusion Medicine, Hannover Medical School. Where indicated, the individuals were identified as carrying wild type or C77G variant CD45. The approval of the local ethical committee was received for this study. PBMCs were prepared by density gradient centrifugation using Biocoll Separating Solution (Biochrom) or Ficoll and cryopreserved until usage. PBMCs were maintained in RPMI 1640 (Biochrom) containing 20 mM Hepes or 1 mM sodium pyruvate, 4 mM glutamine and 10% FCS.

Recombinant adenovirus stocks were produced in 293A cells, essentially as described (Untergasser A, Dumortier J, Oberwinkler H and Protzer U. "Production of Adenoviral Vectors" *Untergasser's Lab*. Spring 2011. http_www_untergasserde/lab/protocols/adeno_vectors_production_v1_0.htm).

Recombinant adenoviruses were titred using a spot assay to identify adenovirus antigens in infected cells as described (Bewig and Schmidt, Biotechniques, 2000 May, 28(5), 870-3), except that 293A cells were used for virus propagation and were fixed using acetone and methanol. Detection antibodies were goat anti adenovirus hexon (Millipore, Darmstadt, Germany) and HRP-conjugated rabbit anti-goat (Dako, Hamburg, Germany), and infected cells were visualised using the Metal Enhanced DAB Substrate Kit (Thermo Fisher Scientific, Bonn, Germany).

Adenovirus Construction

Recombinant adenoviruses based on the AdZ replication deficient adenovirus vector kindly provided by G. Wilkinson, Cardiff University, UK, were constructed by homologous recombination as described (Stanton et al, 2008, *Biotechniques,* 45(6), 659-62, 664-8). RAdV UL11 contains the UL11 open reading frame from the TB40/E strain of HCMV with a C-terminal V5 epitope tag, an IRES element and the eGFP open reading frame. The V5 epitope tag (GKPIPNPLLGLDST) seq. ID. No. 5 was added to the C-terminus of UL11 in the HCMV TB40/E BAC (Sinzger et al, J. Gen Virol, 2008, 89 (Pt2), 359-68) by homologous recombination using ET mutagenesis. The UL11V5 fragment was amplified using the following primer pair: UL11V5IRESfor: 5'-agtcggatccaattacctgtggtagaatgc-3' (Seq. ID. No. 6), UL11V51RESrev: 5'-ggccggatccttacgtagaatcaagaccta-3' (Seq. ID No. 7) and cloned into the pIRES eGFP vector (BD Biosciences Clontech, Heidelberg, Germany).

The UL11V5 IRES eGFP cassette was amplified and an upstream Kozak sequence (underlined) introduced using the following primer pair: UL11V5GFPrAdVfor: 5'-aagacacgggaccgatccagcctggatccgccaccatgctgtt caggtacatcac-3' (Seq. ID. No.8), GFPrAdVrev: 5'-tatagagtatacaatagt-gacgtgggatcctcacttgtacagctcatcca-3' (Seq. ID. No. 9).

The resulting fragment was amplified again using extended primers to introduce sequences with homology to the AdZ vector, using the following primers: rAdVfor: 5'-aaccgtcagatcgcctggagacgccatccacgctgttttgacctccataga agacaccgggaccgatccagcctg-3' (Seq. ID. No.10), radVrev: 5'-ggcgtgacacgtttattgagtaggattacagagtataacatagagtataata-gagtatacaatagtgacgtgg-3' (Seq. ID. No.11).

The amplified fragment was then introduced into the AdZ vector by homologous recombination in the *E. coli* SW102 strain as previously described (Stanton et al 2008, above).

RAdV GFP contains the GFP open reading frame and was constructed by amplifying the GFP gene from the pIRES eGFP vector with an introduced Kozak sequence using the following primer pair, GFPrAdVfor: 5'-aagacaccgggac-cgatccagcctggatccgccccctctccctccc-3' (Seq. ID. No.12) and the GFPrAdVrev primer. This fragment was then amplified using the same extended primer pair, rAdVfor and rAdVrev, as was used for the construction of rAdV UL11 and also introduced into the AdZ vector by homologous recombination. The construction of rAdV UL6Fc is described below under Fc fusion protein production. The correct construction of the adenovirus BACs was confirmed by restriction analysis and sequencing.

Fc Fusion Protein Production

The sequence encoding the predicted extracellular domain of UL11 was amplified from the TB40/E BAC (Sinzger et al) (nt 51260-51865) using the following primer pair UL11 for: 5'-cgggatccatcagcctccacgatgcctg-3' (Seq. ID. No.13), UL11 rev: 5'-ccggtcgactgtagccacgtgttggtgc-3' (Seq. ID. No.14) and ligated into the PCR3 vector (Invitrogen) containing sequences encoding the mouse IgH signal peptide and the Fc region of human IgG1 (Cheung et al, PNAS, 2005, 102(37), 13218-23), kindly provided by C. Benedict, La Jolla Institute for Allergy and Immunology, San Diego, USA. The UL11Fc open reading frame was then amplified using the following primers, UL11Fcfor: 5'-cggcggccgc gccaccatgaacttcgggttc-3' (Seq. ID. No.15), Fcrev: 5'-cggaat- tctcatttacccggagacaggg-3' (Seq. ID. No.16) allowing the insertion of an upstream Kozak sequence (underlined), and ligated into the pSFbeta91-wpre replication deficient retro- virus vector, kindly provided by J. Bohne, Hannover Medi- cal School, Germany (Hildinger et al, J. Virol., 1999, 73(5), 4083-9). The open reading frame encoding the Fc domain of human IgG1 was amplified using the following primers Fcfor: 5'-cggcggccgcgccaccatgaacttcgggttc-3' (Seq. ID. No.17), and Fcrev: 5'-cggaattctcatttacccggagacaggg-3' (Seq. ID. No.18) and also ligated into the pSFbeta91-wpre vector. Retroviruses were constructed by transfecting the pSF- beta91-wpre constructs into the Phoenix-gp packaging cell line together with the retroviral gag/pol plasmid M25-DAW (Schambach et al, Gene Ther. 2006, 13 (21), 1524-33) and the feline endogenous retrovirus envelope glycoprotein expression plasmid RD114 (Cosset et al, J. Virol., 1995, 69(12), 7430-6) and used to tranduce 293T cells.

The predicted extracellular domain of UL6 was amplified from the TB40/E BAC (nt 47410-48124) and ligated into the PCR3 vector containing sequences encoding the mouse IgH signal peptide and the Fc region of human IgG1 using the following primer pair: 5'-cgggatcccatgctaagataaacgggtgg-3' (Seq. ID. No.19), 5'-ccggtcgacgaatgccaagttagttatgttc-3'(Seq. ID. No.20).

The UL6-Fc open reading frame was then amplified using the following primer pair, Forward: 5'-aag aca ccg gga ccg atc cag cct gga tcc gccacc atg aac ttc ggg ttc-3'(Seq. ID. No.21), Reverse: 5'-tat aga gta tac aat agt gac gtg gga tcc tca ttt acc egg aga cag gga gag-3'(Seq. ID. No.22) allowing the insertion of an upstream Kozak sequence (underlined). A second round of amplification was then performed using the same extended primer pair, rAdVfor and rAdVrev, as was used for the construction of rAdV UL11 and rAdV GFP. The resulting product was recombined into the AdZ adenovirus vector as described above.

The UL11Fc, UL6 and Fc control proteins were purified from serum free supernatants of retrovirally transduced 293T cells or adenovirally transduced RPE cells by protein A affinity chromatography using hiTrap rProtein A FF col- umns (GE Healthcare, Munich, Germany).

UL11 Antiserum Production

The UL11Fc protein was provided to the Pineda Antiko- erper Service, Berlin, Germany, for the inoculation of rab- bits. Antiserum was preadsorbed before use. Briefly, A549 cells were incubated with blocking solution (1% BSA, 0.1% gelatine, PBS) for 30 min, followed by a 1:2 dilution of UL11 antiserum in blocking solution for 8 h at 4° C. Cell debris was removed by centrifugation and 0.1% $NaN_3$ added.

Flow Cytometry Analysis

Cell surface expression of UL11 was measured in adeno- virus transduced HFF or A549 cells, 72 hpi. HFF cells were transduced with a MOI of 500, A549 cells with a MOI of 300. Cells were incubated with UL11 antiserum or pre- immune serum in surface blocking solution (1% BSA, 0.1% gelatine, 2 mM EDTA in PBS) followed by PE-conjugated goat anti-rabbit antibody (Open Biosystems, Bonn, Ger- many) in blocking solution containing 6% goat serum. All steps were performed at 4° C.

For flow cytometry based binding assays to PBMCs, 2.5 µg of purified Fc fusion proteins were incubated with $1 \times 10^6$ cells in blocking solution (5% mouse serum, 2 mM EDTA in PBS). Bound protein was detected using phycoerythrin (PE) conjugated anti-human IgG (Acris, Herford, Germany). Sub-populations of PBMCs were identified using antibodies directed to the following surface markers; T cells: anti-CD3- FITC (Immunotools, Friesoythe, Germany), anti-CD4- Dy647 (Acris), anti-CD8-PE-Dy590 (Antibodies-online, Aachen, Germany). B cells: anti-CD19-PE-Dy590 (Anti- bodies-online). NK cells: anti-CD56-APC (Immunotools, Friesoythe, Germany); NK cells were identified as CD56 positive and CD3 negative cells, monocytes: anti-CD14- APC (Immunotools) and granulocytes: anti-CD15-FITC (BD, Heidelberg, Germany).

Intracellular levels of pY505 lck were measured follow- ing treatment with Fc fusion proteins: $1.25 \times 10^5$ Jurkat cells per well were incubated for 1 h in MaxiSorb 96 well plates (Nunc, Langenselbold, Germany), pre-coated with 2.5 µg Fc fusion protein per well. Cells were then incubated in block- ing buffer (6% goat serum, 2 mM EDTA in PBS), permea- bilised using 0.1% saponin in blocking buffer and stained using rabbit anti-lck pY505 (Cell Signalling Technology, Danvers, USA) and anti-rabbit-Alexa 488 (Invitrogen, Darmstadt, Germany). Measurements were performed on a Beckmann Coulter Cytomics FC500 cytometer and analysed using CXP analysis software.

FACS based binding assays to stimulated CD4 T cells were performed using CD4 T cells prepared from PBMCs from control or variant (CD45 C77G) donors by MACS separation (Miltenyi Biotec, Bergisch Gladbach, Germany). Briefly, cells were incubated with the OKT-4 anti-CD4 mAb (purified from hybridoma) for 30 min on ice, washed twice and incubated with anti-mouse antibody-coupled magnetic beads for a further 15 min on ice. Magnetically labelled CD4 positive cells were retained in a magnetic separating column and non-labelled cells washed away. The purity of the CD4 positive fraction was determined by FACS. Sorted cells were stained and measured immediately or were stimulated with 1 µg/ml PHA (Murex Diagnostics Ltd., Dartford, UK) for 24 h and then treated for 8 days with 25 U/ml Il-2 (Hoffmann- La Roche, Basel, Switzerland). For staining, the cells were incubated for 20 minutes in 50% mouse serum in PBS, followed by Fc fusion protein (1 µg) for a further 45 minutes. After washing, cells were incubated for 20 minutes with antibodies specific for long and short isoforms of CD45; FITC-conjugated anti-CD45RA and APC-conjugated anti- CD45R0 (BD, Heidelberg, Germany). Bound Fc fusion proteins were detected using PE-conjugated anti-human IgG (Acris, Herford, Germany). Measurement was performed using a FACSCalibur cytometer (BD) and analysis was performed using WinMDI software, version 2.9.

Fluorescence Microscopy

To detect surface expression of UL11, A549 or HFF cells were grown on glass coverslips and infected with rAdVs at MOIs of 300 and 500 respectively. At 72 hpi, cells were incubated with preadsorbed anti UL11 serum in blocking solution (1% BSA, 0.1% gelatine, PBS) for 1 hour at 4° C., followed by Alexa 568 conjugated goat anti-rabbit (Invitro- gen, Darmstadt, Germany). Cells were fixed with 3% PFA and observed using a Zeiss LSM 510 Meta Confocal Micro- scope.

To observe leukocyte resetting, primary human foreskin fibroblasts (HFF) were infected with RadVs at a MOI 500. At 96 hpi HFFs were co-cultured with Jurkat T cells, J(AS-1) T cells or primary freshly isolated PBMCs at a ratio of 1:20 for 2 hours at 37° C., washed 8 times with PBS and observed using a Zeiss Axio Observer light/epifluorescent microscope.

Deglycosylation, Biotinylation, Pull-Downs, Silver Staining and Western Blot Analysis The glycosylation state of UL11 was investigated using purified UL11Fc or lysates of A549 cells transduced with rAdV with MOI 100, 72 hpi, prepared with NP40 lysis buffer (150 mM NaCl, 1% NP40, 10 mM Tris-HCl pH 7.4, 1 mM EDTA, protease inhibitor cocktail (Calbiochem, Darmstadt, Germany)). Cell lysates or purified proteins were boiled for 5 min in denaturing buffer (0.5% SDS, 0.5% 2-mercaptoethanol) before being treated with N-glycosidase F (Roche, Grenzach-Wyhlen, Germany) or Endo-α-N-acetylgalactosaminidase and neuraminidase (New England Biolabs, Frankfurt am Main, Germany) in 500 mM sodium phosphate buffer pH 7.6 containing 1% NP40 for 2 hours or overnight at 37° C.

Cell surface proteins were biotinylated by incubating $2.5 \times 10^7$ cells/ml in PBS with 2 mM Sulfo-NHS-LC-Biotin (Thermo Fisher Scientific, Bonn, Germany), for 30 min. The cells were washed three times with 100 mM glycine in PBS and then lysed in NP-40 lysis buffer.

Proteins were pulled down or immunoprecipitated from cell lysates prepared from $1 \times 10^8$ cells/ml of NP40 lysis buffer. 500 µl of cell lysate was precleared with protein A sepharose CL-4B (GE Healthcare, Munich, Germany) and then incubated with 10 µg of Fc fusion protein or antibody and 20 µl protein A sepharose for 90 min at 4° C. CD45 was immunoprecipitated using MEM-28 (Immunotools, Friesoythe, Germany) and CD3 using OKT3 (eBioscience, Frankfurt, Germany). Protein A sepharose was then washed three times in lysis buffer.

Proteins in SDS-PAGE gels were visualised by silver staining; gels were washed twice in fixer 1 (50% methanol, 10% acetic acid) for 15 min each, once in fixer 2 (10% ethanol, 5% acetic acid) for 6 min, and rinsed twice for 9 min in water. Gels were then incubated in sensitiser (20 mg/l sodium hydrosulfite) for 9 min, followed by silver solution (0.1% silver nitrate, containing 0.75 µl/ml 37% formaldehyde) for a further 9 min. Gels were then rinsed for 30 s in water and transferred to image developer (3% sodium carbonate containing 1 µl/ml 37% formaldehyde and 1 µl/ml of a 10 g/l sodium thiosulfate solution). Development was halted using stop solution (2.5% acetic acid, 5% Tris).

UL11 was detected by immunoblotting in lysates prepared from adenovirus transduced A549 cells with MOI of 100, 72 hpi, lysed in NP40 lysis buffer. Proteins were separated by SDS PAGE, transferred to Hybond ECL nitrocellulose membranes (GE Healthcare, Munich, Germany) and UL11 detected using mouse anti-V5 antibodies (Invitrogen, Darmstadt, Germany) or rabbit anti-UL11 serum followed by HRP-conjugated anti-mouse or anti-rabbit antibodies (Dako, Hamburg, Germany). CD45 was visualised using the MEM-28 anti-CD45 antibody (Immunotools, Friesoythe, Germany). Phosphotyrosine proteins were detected using the 4G10 anti-phosphotyrosine antibody (Millipore, Darmstadt, Germany).

T Cell Stimulation; Tyrosine Phosphorylation and Cell Proliferation

Induction of tyrosine phosphorylation was measured after the incubation of Fc fusion proteins (2.5 µg) with $2 \times 10^6$ Jurkat cells in 200 µl of culture medium for 30 minutes at 37° C. The cells were then stimulated with 1 µg of the anti-CD3 antibody (OKT3), (eBioscience, Frankfurt, Germany) and 3 µg of goat anti-mouse antibody (Dianova, Hamburg, Germany) to cross-link the OKT3. Stimulation was stopped by the addition of 500 µl ice-cold stop solution (5 mM EDTA in PBS) and the cell suspension was immediately centrifuged. The cell pellet was then lysed with NP-40 lysis buffer (1% NP-40, 25 mM Tris-HCl pH 8.0, 150 mM NaCl, 2 mM sodium vanadate, 5 mM EDTA and protease inhibitor cocktail (Calbiochem, Darmstadt, Germany).

Intracellular levels of pY505 lck were measured following treatment with Fc fusion proteins: $1.25 \times 10^5$ Jurkat cells per well were incubated for 1 h in MaxiSorb 96 well plates (Nunc, Langenselbold, Germany), pre-coated with 2.5 µg Fc fusion protein per well. Cells were then incubated in blocking buffer (6% goat serum, 2 mM EDTA in PBS), permeabilised using 0.1% saponin in blocking buffer and stained using rabbit anti-lck pY505 (Cell Signalling Technology, Danvers, USA) and anti-rabbit-Alexa 488 (Invitrogen, Darmstadt, Germany).

To investigate the effect of soluble UL11 on PBMC proliferation, Fc fusion proteins (2.5 µg) and OKT3 (1 µg), which was purified from hybridoma supernatants in the Department of Clinical Immunology, Hannover Medical School, were adsorbed onto Maxi-Sorb 96-well plates (Nunc, Langenselbold, Germany). $1 \times 10^5$ PBMCs per well were incubated in 200 µl of culture medium. PHA (Oxoid, Basingstoke, UK) was added where indicated at 25 µg/ml. After 48 h, 0.4 µCi [$^3$H]thymidine (Amersham Biosciences, Braunschweig, Germany) was added. After 24 h the cells were harvested and incorporated [$^3$H]thymidine measured in a beta-counter (Perkin Elmer, Rodgau, Germany).

Tryptic Digestion and Mass Spectrometric Analysis

Spots were excised manually with from a preparative, coomassie-stained gel. After destaining two times with 100 µL of 50% acetonitrile (ACN), 20 mM $NH_4HCO_3$ at 37° C. for 30 min, spots were dehydrated by adding 100 µL ACN and dried. Twenty micro liter of 10 ng/mL sequencing grade trypsin (Promega) were added and after 30 min incubation on ice remaining trypsin solution was discarded. Digestion was continued at 37° C. over night and stopped by adding 0.1% TFA, 50% ACN. Tryptic peptides were extracted with two times 20 µL 50% ACN, 0.1% formic acid (FA) for 30 min at 37° C. and 10 µL ACN for 30 min at RT. All extracts were combined and dried in a vacuum centrifuge.

For LC-iontrap-MS analysis peptide samples were dissolved in 10 µL 10% ACN. Five microliter per peptide sample were injected onto a C18 RP-Column (Zorbax SB, C18, 80 Å, 5 µm, 150×0.5 mm, Agilent) using a 1100 Series Agilent HPLC System equipped with an autosampler, coupled online to an Esquire3000+ ion trap mass spectrometer (Bruker Daltonics). Using a two buffer system (A: 5% ACN, 0.1% FA; B: 80% ACN, 0.1% FA) and a flow rate of 5 µL/min, a multi-step gradient was applied after injection: 0-5 min: 0% B; 30 min gradient to 53.9% B (40% ACN); 5 min gradient to 100% B; increase of flow rate to 10 µL/min in 1 min; 10 min at 100% B; 4 min gradient to 0% B; 15 min at 0% B.

The MS method used to select and fragment the eluting peptides was set to trigger fragmentation of the three most intensive peaks from an MS scan at a 10,000 ion count threshold and a preference of doubly charged ions. Automated precursor exclusion after one acquired spectrum per precursor for 0.3 min was used. The ESI source conditions were set to 10 psi nebulizer gas pressure with dry gas heated to 300° C. at a flow rate of 4.0 L/min.

Mass spectrometrical data were searched against the SwissProt Database with carbamidomethylation of cysteins as static and oxidation of methionine as variable modification. For ion trap-MS 150 ppm mass deviation was tolerated for precursors and 0.7 Da for peptide fragments in MS/MS.

At least two peptides with a Mascot peptide ion score higher than 25 each were used as a threshold for protein identification.

Results:

| Protein | # of peptides | Sequence coverage | size receptor tyrosine phosphatase |
|---|---|---|---|
| CD45 | 8 | 5% | 131 kDa |

UL11 is a Surface Expressed Glycoprotein

UL11 is predicted to be a type I transmembrane protein (FIG. 1A) and has previously been reported to be expressed on the surface of HEL fibroblasts infected with the highly passaged AD169 laboratory strain of HCMV. To allow us to work with conveniently detectable levels of UL11, we therefore used an adenovirus expression system.

Figure 8:
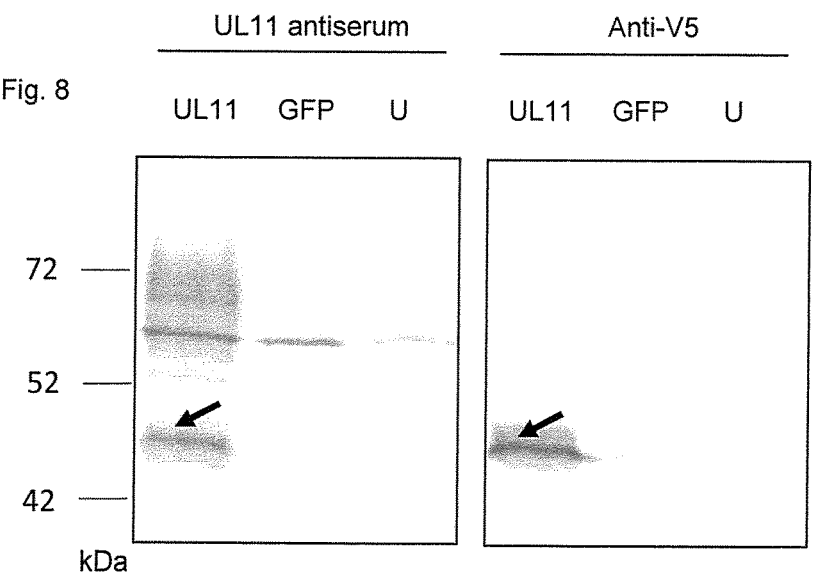
FIG. 8 Rabbit antiserum raised against the predicted extracellular domain of UL11 detects an approximately 50 kD protein in transduced cells. The predicted extracellular domain of UL11 fused to the human IgG Fc domain (FIG. 9) was used to immunize rabbits. Serum was pre-absorbed with rAdV GFP transduced cells to reduce non-specific interactions. Lysates of A549 cells transduced with rAdV UL11 (UL11), rAdV GFP (GFP), or left uninfected (U) were used to prepare immunoblots and proteins were detected using UL11 anti-serum and a HRP-conjugated anti-rabbit secondary antibody, or antibody specific for the V5 epitope. Bands corresponding to UL11 are indicated.

We constructed a recombinant adenovirus expressing UL11 from the TB40/E strain of HCMV with the Simian Virus 5 V5 epitope at the C-terminus and GFP as a separate protein to allow the identification of transduced cells (rAdV UL11). Using a polyclonal antiserum specific for the predicted N-terminal extracellular domain of UL11 (FIG. 8) we could detect UL11 on the surface of A549 lung epithelial cells and HFF cells transduced with rAdV UL11, but not with a control GFP expressing adenovirus lacking UL11 (rAdV GFP), by FACS (FIG. 1B) and confocal microscopy (FIG. 1C). The surface expression of UL11 is therefore not dependent on the strain of HCMV or on the cell type used and does not require the presence of other HCMV proteins. To characterise the UL11 protein, we transduced A549 cells with rAdV UL11 and performed immunoblots of the cell lysates using an antibody specific for the V5 epitope (FIG. 1D). The predicted molecular weight of UL11 is 31 kDa, but the protein migrates at approximately 50 kDa on a polyacrylamide gel. To investigate potential glycosylation of UL11, adenovirus transduced cell lysates were treated with Peptide N-Glycosidase F (PNGase F), or Endo-α-N-Acetylgalactosaminidase (O-glycosidase), or a combination of the two and immunoblotted (FIG. 1E). PNGase F treatment increased the speed of migration of UL11 to approximately the predicted 31 kDa, but treatment with O-glycosidase, either alone or in combination with PNGase F, had no effect. N-linked glycosylation therefore appears to form all or the majority of the posttranslational modification of UL11.

The Extracellular Domain of UL11 Interacts with a Leukocyte Cell Surface Component As UL11 is expressed on the cell surface, its role could potentially be to interact with proteins on the surface of neighbouring cells. We therefore measured interactions between the extracellular domain of UL11 and different cell types. The UL11 extracellular domain was cloned as a fusion with the Fc domain of human IgG at the C-terminus and the cleavable mouse IgH signal peptide at the N-terminus (FIG. 9A). The UL11Fc fusion protein was expressed and secreted from transduced 293T cells and then purified by affinity purification using protein A sepharose (FIG. 9B). Expression of UL11Fc was performed in eukaryotic cells to preserve the N-linked glycosylation seen in the full-length protein, as this could influence interactions with ligands. Treatment of UL11Fc with PNGase F resulted in a change in migration rate from 95 kDa to 70 kDa (FIG. 9D). PNGase F treatment of the Fc domain alone produced a reduction in size of 5 kDa. The degree of glycosylation attributable to the UL11 part of the fusion protein of approximately 20 kDa is therefore similar to that seen in the full-length protein (FIG. 1E). The purified UL11Fc protein was incubated with five different cell lines; HeLa, 293T, BJ fibroblasts, BJAB and Jurkat, and interactions were detected by FACS using a phycoerythrin (PE)-coupled antibody specific for the Fc domain. Binding of UL11Fc was compared with that of the Fc domain alone (FIG. 2A). Interactions could be seen between UL11Fc and the leukocyte cell lines BJAB and Jurkat but not with the non-haematopoietic cell lines HeLa, 293T or BJ fibroblasts. The study was then expanded to include primary cells. PBMCs were isolated from blood from a healthy donor by separation over a Ficoll gradient. Binding of UL11Fc to different leukocyte subsets, identified by cell surface antigens and cell size, was investigated by FACS (FIG. 2B). Interactions with UL11Fc could be detected with all cell types tested; CD4 T cells, CD8 T cells, B cells, NK cells, monocytes and neutrophils.

UL11 Interacts with a 200 kD Protein

To identify interaction partners of UL11, experiments were made to precipitate interacting proteins from Jurkat cell lysates. As no detectable binding of UL11Fc to 293T cells had been observed, (FIG. 2A) 293T cell lysates were used as a negative control. Lysates or lysis buffer were incubated with UL11Fc or the Fc domain alone and the Fc proteins and their interaction partners were precipitated by the addition of protein A sepharose, separated by gel electrophoresis and visualised by silver staining (FIG. 3A). A doublet of approximately 200 kDa and several smaller proteins were precipitated by UL11Fc from Jurkat cell lysates, but not from 293T cell lysates. The absence of the 200 kDa doublet in the sample containing only lysis buffer, but no cell lysate, indicated that the doublet was not an artefact caused, for instance, by dimerisation of the input UL11Fc protein. The bands were not detectable when the Fc domain alone was used as bait.

Although UL11 may also interact with intracellular proteins, we wished to identify the surface glycoprotein responsible for the interaction of UL11 with lymphocytes. To determine which of the proteins precipitated from Jurkat lysates were surface proteins, intact Jurkat or 293T cells were first labelled with membrane impermeable biotin and then lysed. The biotinylated lysates were incubated with UL11Fc, the Fc domain alone, or an antibody specific for the ε-chain of CD3 and protein A sepharose. After separation by electrophoresis and blotting, precipitated surface proteins could be detected using HRP-coupled streptavidin (FIG. 3B). A 23 kDa protein was immunoprecipitated by the anti-CD3-ε antibody, as predicted. The 200 kDa doublet produced the strongest signal of the proteins precipitated by UL11Fc and was not detectable in lysates incubated with the Fc domain, or the anti-CD3-ε antibody. The doublet was also not produced from the sample containing biotinylated 293T cell lysate.

To identify the protein, the experiment was repeated using a larger number of cells, and the doublet was subjected to mass spectrometric analysis. Eight peptides stemming from CD45 were detected, and no other peptides corresponding to surface proteins.

UL11 Interacts with CD45

Figure 4:
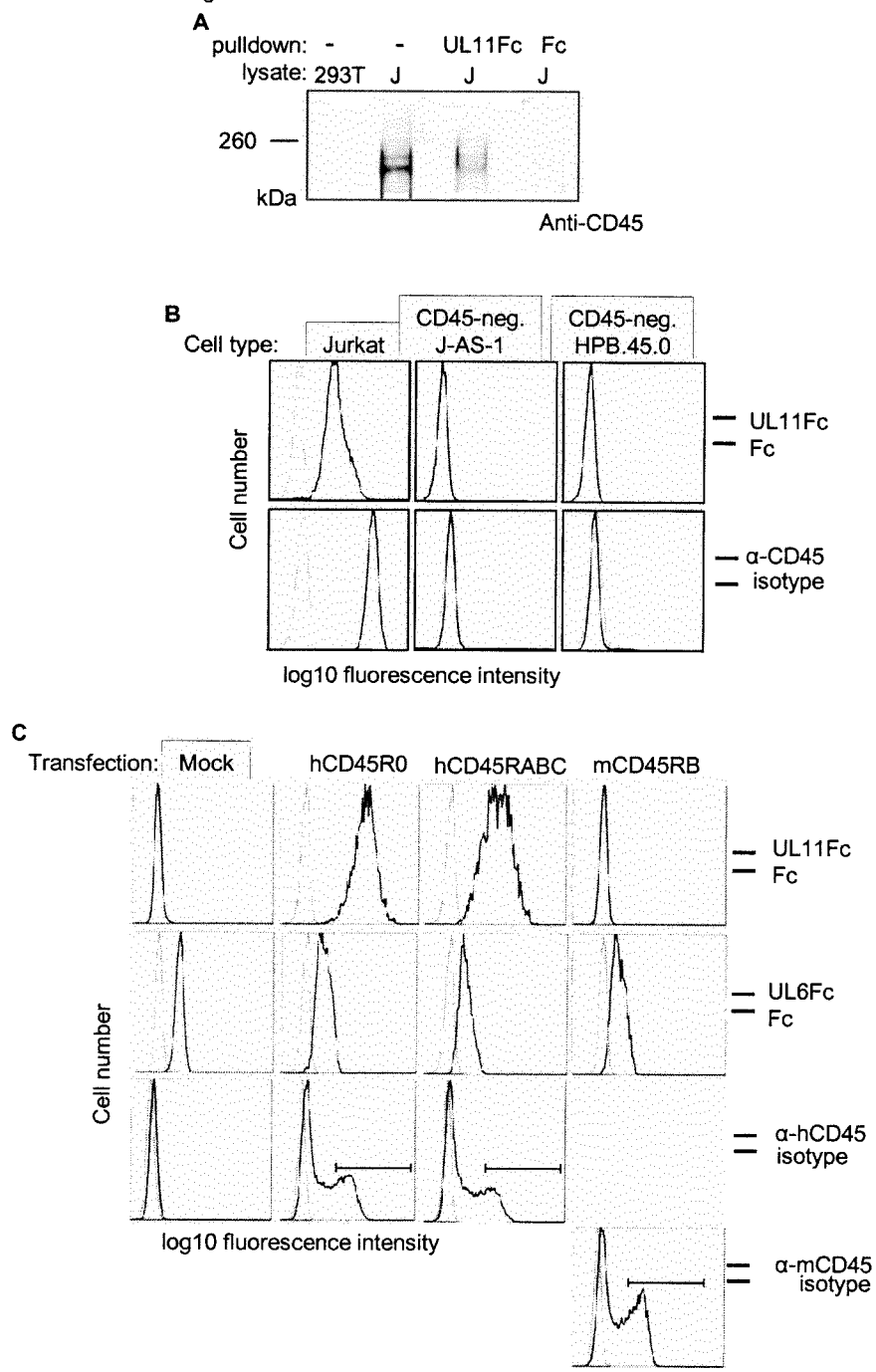
FIG. 4. UL11 interacts with CD45. A) Proteins interacting with UL11Fc or the Fc domain were precipitated from 293T or Jurkat (J) cell lysates, as in FIG. 3. After blotting, CD45 was detected using anti-CD45. B) UL11Fc or the Fc domain were incubated with Jurkat cells or T cell lines lacking CD45 (upper panel) and detected as in FIG. 2. Black lines represent UL11Fc binding, grey lines the Fc domain. CD45 expression is shown (lower panel) using PE-coupled anti-CD45. Black lines show anti-CD45, grey lines an isotype control. C) 293T cells were transfected with plasmids encoding either the human CD45RABC or CD45R0 isoforms, mouse CD45RB, or mock transfected. 48 h post transfection, the cells were incubated with UL11Fc, UL6Fc or the Fc domain and costained with PE-labelled anti-IgG and FITC-labelled anti-human (h) or mouse (m) CD45. Binding of UL11Fc, UL6 or Fc to CD45 expressing cells is shown (upper panels; UL11Fc and UL6Fc in black, Fc domain in grey). Expression of hCD45 or mCD45 is shown in the lower panels.

To confirm the interaction of UL11 with CD45 detected by mass spectrometric analysis, the protein precipitated from Jurkat cell lysates by UL11Fc was analysed by immunoblotting with an antibody against CD45 (FIG. 4A). CD45 protein could be detected in UL11Fc treated Jurkat lysates, but not in 293T cell lysates, or in proteins precipitated from Jurkat cell lysates by the control Fc domain. This confirms that the extracellular domain of UL11 can interact with CD45 in Jurkat cell lysates and that the interaction is specific for UL11.

CD45 is expressed on the surface of all nucleated haematopoietic cells and could therefore be the interaction partner of UL11 seen by FACS analysis of leukocytes. We analysed the interaction of UL11 with T cell lines that do not express CD45. The J-AS-1 cell line is a Jurkat cell line in which CD45 expression has been selectively reduced by the stable expression of antisense RNA. HPB.45.0 is a HPB-ALL derived T cell line selected for lack of CD45 expression (Koretzky, et al., 1990, Nature 346:66-68) In both of these cell lines, the lack of CD45 expression and the corresponding lack of UL11 binding could be seen by FACS (FIG. 4B). To show that CD45 expression is sufficient to induce the interaction of UL11 with a cell, we expressed two isoforms of CD45 in 293T cells by transient transfection. In both cases, an interaction of UL11 with the cells expressing CD45 could be seen (FIG. 4C). As an additional control, we expressed and purified a second member of the RL11 family, UL6, as an Fc fusion protein (FIG. 9). The binding profile of UL6 in FACS experiments is different from UL11; UL6 binds to untransfected 293T cells and its binding is not affected by transfection with either of the CD45 isoforms (FIG. 4C).

UL11 Interacts with Both Long and Short Isoforms of CD45

Five different isoforms of CD45, generated by variation in splicing, have been detected in human lymphocytes. The expression of these isoforms is tightly controlled, depending on cell type, stimulation and maturation (Hermiston, et al., 2003. Annu. Rev. Immunol. 21:107-137). Naïve T cells typically express high molecular weight isoforms of CD45 that are no longer detectable after stimulation. In individuals with a variant form of CD45, typified by the C77G polymorphism, the splicing pattern of CD45 is altered, meaning that cells expressing both long and short isoforms of CD45 are present after stimulation. To analyse UL11 binding, primary T cells from both types of individuals were stained with antibodies against CD45 and coincubated with UL11Fc (FIGS. 5A and B). Binding could be seen to all populations of CD45 positive cells. Upon stimulation of the cells with mitogen, the CD45 expression pattern changed, but UL11 binding was not affected (FIGS. 5A and B). This indicates that UL11 can interact with both naïve and mature T cells.

UL11 Disrupts T Cell Signalling Though p56$^{lck}$ and Inhibits Proliferation

CD45 functions to permit T cell receptor signalling, enabling T cell activation and proliferation. Stimulation through CD3 activates a signalling cascade resulting in the increased tyrosine phosphorylation of many proteins. To investigate the effect of UL11 on this function of CD45, we stimulated Jurkat T cells in the presence and absence of UL11Fc and detected changes in tyrosine phosphorylation by immunoblotting using an antibody recognising phosphotyrosines. In untreated cells, and cells preincubated with the Fc control protein, an increase in tyrosine phosphorylation was readily detectable upon CD3 stimulation. In cells preincubated with UL11, however, this increase was no longer seen (FIG. 6A), indicating an inhibitory effect of UL11 on T cell signalling.

The controlling effect of CD45 on T cell signalling is exerted via changes in phosphorylation of the src family kinase lck. CD45 dephosphorylates the tyrosine 505 residue of lck, resulting in the production of an active form of lck that enables signalling through the TCR. To determine whether the effect of UL11 is to disrupt the action of CD45 on its substrate, measurements of the extent of phosphorylation of Y505 of lck by intracellular FACS were performed (FIG. 6B). In both cases, pretreatment with UL11Fc increased the amount of inactive lck in the cells.

An outcome of signalling through the T cell receptor is that T cells proliferate. To determine whether T cell proliferation is also disrupted by UL11 treatment, we measured the effects of UL11Fc on the proliferation of primary T cells in response to stimulation via the TCR (FIG. 6C). T cells were incubated in plates coated with the OKT3 anti-CD3 antibody or with the mitogen phytohaemagglutinin (PHA), in the presence of UL11Fc, the control Fc domain or BSA. After 72 h, the incorporation of tritiated thymidine was determined, as a measure of proliferation. UL11 inhibited proliferation resulting from both OKT3 and PHA stimulation.

Cell Surface Expressed UL11 Mediates Intercellular Interactions

Figure 7:
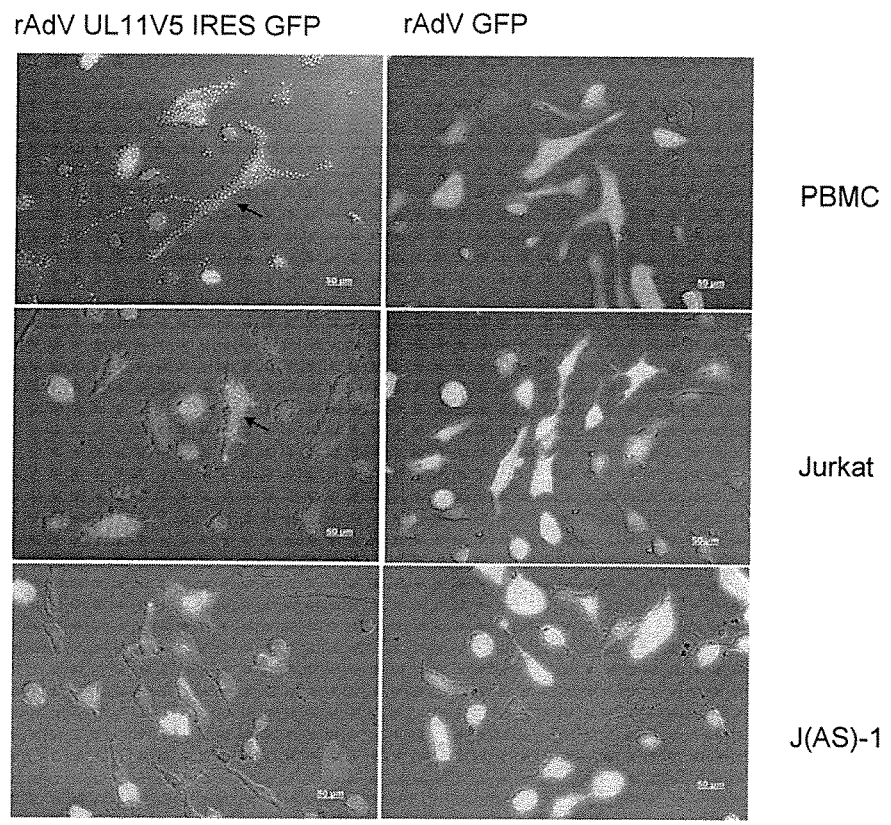
FIG. 7. Surface expressed UL11 mediates cell adhesion HFF cells were transduced with recombinant adenoviruses expressing UL11 and GFP (rAdV UL11V5 RES GFP) or GFP alone (rAdV GFP). 3 days after transduction, PBMCs, Jurkats or J(AS)-1 cells were incubated with the fibroblasts for 2 h and then unbound cells removed by washing. White arrows indicate adhering cells, green cells show adenovirus derived GFP.

We were interested in whether the complete, surface expressed UL11 protein also has adhesion and inhibitory properties. To investigate this question, we transduced HFF cells with rAdV UL11 or the control rAdV GFP adenovirus and incubated these presenter cells with PBMCs, Jurkat or J(AS)-1 cells lacking Cd45 (FIG. 7A). After washing away the unbound cells, rosetting of PBMCs and Jurkat cells around the UL11 expressing cells could be clearly seen, and was absent from the control cells. No resetting of the J(AS)-1 cells was seen, indicating requirements for both CD45 and UL11 for the interaction to take place.

Discussion

UL11 is a member of the human cytomegalovirus RL11 gene family. RL11 proteins share the RL11 domain, a variable region of between 65 and 82 residues that has some sequence homology to the adenovirus CR1 domain and to immunoglobulin domains. This homology led us to investigate potential immunomodulatory properties of UL11.

We showed that the UL11 protein from the TB40/E strain of HCMV is expressed on the surface of fibroblasts and endothelial cells, in agreement with previously published data describing the detection of UL11 on the surface of HEL fibroblasts infected with the highly passaged laboratory strain of HCMV, AD169. Proteins from the RL11 family are predicted to be glycosylated; UL4 and RL11 have been shown to possess N-linked glycans, and we also showed this to be the case for UL11.

The extracellular domain of UL11 was used in FACS binding studies and interacted with leukocyte cell lines and primary leukocytes, but not with control cell lines. Mass spectrometry analysis of interacting Jurkat surface proteins identified CD45 as a binding partner of UL11 in Jurkat cell lysates. That CD45 is also responsible for the interaction of UL11 with leukocytes seen in FACS analysis was confirmed using two different CD45 deficient cell lines. Transfection of CD45 into 293T cells induced UL11 binding, indicating that CD45 expression is sufficient for the interaction. A second member of the RL11 family, UL6, was used to investigate whether the interaction with CD45 is a general property of RL11 proteins, or specific to UL11. No changes in UL6 binding were seen in relation to CD45 expression, indicating that the interaction is a particular property of UL11. The interaction of UL11 with the surface of leukocytes could also be demonstrated using full-length UL11 expressed on the surface of fibroblasts, to which PBMCs and CD45 expressing T cells adhered. CD45 exists as a set of different isoforms, the expression and glycosylation of which is tightly controlled and depends on cell type and maturation state. We demonstrated that UL11 binds to both long and short isoforms of CD45, and to both naïve and mature T cells.

The interaction of UL11 with CD45 is markedly different from that of other known CD45 ligands. The other CD45 ligands that have been described are all lectins, which interact with a variety of glycosylated lymphocyte cell surface proteins and typically have marked differences in their interactions with the various UL11 isoforms and glycoforms due to their differing glycosylation patterns. UL11 appears to bind selectively to CD45 and interacts with both long (RABC) and short (R0) isoforms of CD45 and to naïve and mature T cells. It therefore seems that the interaction of UL11 with CD45 is of a different nature from previously described interactions. The C-type lectin macrophage galactose type lectin (MGL), a pattern recognition receptor on myeloid antigen presenting cells which recognises GalNAc sugars, for example, binds only to the longer isoforms of CD45 due to their higher GalNAc content, and also to the sialoglycoprotein CD43. The B-cell Siglec lectin CD22, which interacts with a wide variety of glycoproteins, binds preferentially to the CD45R0 isoform in trans, as this isoform possesses the necessary N-glycans decorated with α(2,6)-linked sialic acid. Other lectins are even more specific in their interactions; glucosidase II and serum-mannan binding protein only interact with CD45 glycoforms characteristically found on immature thymocytes; in the case of S-MBP only with the hybrid-type N-linked glycans on the R0 isoform.

Galectin-1 binds to at least six glycoproteins on the surface of T-cells, including CD45, via poly (N-acetyllactosamine), found on CD45 only in DP thymocytes and activated peripheral CD4+ Th1 cells. As we have not identified CD45 isoforms that do not interact with UL11, it seems likely that the effects of UL11 could be more far reaching than the lectins so far described, and also more selective as UL11 appears to interact specifically with CD45.

CD45 is necessary for T cell function. The src family kinase Lck is activated by CD45-mediated dephosphorylation of its activating residue tyrosine 505. In the absence of active Lck, signal transduction through the T cell receptor is disrupted. The binding of UL11 to T cells affects signalling in ways indicative of an inhibition of CD45 function. Pretreatment with soluble UL11 restricts the cascade of tyrosine phosphorylation triggered by T cell stimulation by anti-CD3. TCR dependent T cell proliferation is also inhibited by both soluble and cell surface expressed UL11. The CD45 substrate Lck must be dephosphorylated at tyrosine 505 to activate signalling cascades, and increases in pY505 Lck are characteristic of reduced CD45 function. Preincubation of T cells with UL11 increases the levels of pY505 lck.

The control of signalling thresholds by CD45 implies that its effects must be tightly regulated, but the regulation of CD45 activity is incompletely understood and fraught with controversy. Regulation by means of homodimerisation has been discussed, and also as a result of changes in the localisation of CD45 with respect to its substrates. Exclusion of CD45 from SMACs by virtue of lipid raft movements has been described. The extracellular domain of CD45 is required for optimal TCR signalling, although not for intrinsic phosphatase activity. Although the existence of a specific regulating ligand remains unknown, functional effects mediated by the interactions of lectins with the extracellular domain of CD45 have been observed, indicating that ligand mediated regulation may occur. The lectin MGL, for example, is expressed on myeloid APCs, where it has a possible immunomodulatory role.

UL11 has been identified as a novel, specific interaction partner of CD45, representing a new pathway by which HCMV can induce immunosuppression. UL11 has therapeutic potential in the treatment of immune system disorders and inflammation, and further investigations will lead to new insights into CD45 function and means of regulation.

The interaction of pUL11 with CD45 is markedly different from that of other known CD45 ligands. The other CD45 ligands that have been described are all lectins, which recognize oligosaccharide moieties with specificities determined by the lectin carbohydrate recognition domains. Lectins typically bind to multiple ligands and have pronounced differences in their interactions with the various CD45 isoforms and glycoforms due to their differing glycosylation patterns. The C-type lectin macrophage galactose type lectin (MGL), a pattern recognition receptor on myeloid antigen presenting cells which recognizes N-acetylgalactosamine (GalNAc) sugars, for example, binds only to the longer isoforms of CD45 due to their higher GalNAc content, and also to the sialoglycoprotein CD43. Other lectins are even more specific in their preferences; glucosidase II and serum-mannan binding protein only interact with CD45 glycoforms characteristically found on immature thymocytes; in the case of serum-mannan binding protein only with the hybrid-type N-linked glycans on the R0 isoform. Lectin ligands for CD45 frequently do not show reduced surface binding to CD45 negative T cell lines, due to the abundance of other suitably glycosylated ligands, and in contrast to the binding pattern observed for pUL11. As pUL11 interacts with diverse forms of CD45 and shows no detectable binding to CD45 negative T cells, its interaction with CD45 seems to be of a different nature from those of previously described ligands. In addition, UL11 has building activities to all isoforms of CD45 while the vast majority of antibodies directed against CD45 react with one isoform of CD45 only.

The invention claimed is:

1. A composition comprising
   i) a recombinant protein comprising at least the extracellular domain of a human cytomegalovirus UL11 protein but not containing a transmembrane region of said human cytomegalovirus UL11 protein, wherein said recombinant protein is able to bind to CD45 and is an immunosuppressor,
   ii) a heterologous molecule of interest linked with the UL11 domain, and
   a physiologically acceptable carrier.

2. The composition according to claim 1, wherein said human cytomegalovirus UL11 protein:
   (i) comprises the amino acid sequence of SEQ ID NO: 2 or SEQ ID NO: 4,
   (ii) is encoded by the nucleic acid sequence of SEQ ID NO: 1 or SEQ ID NO: 3, or (iii) comprises the amino acid sequence of SEQ ID NO: 2 or 4, wherein said sequence is modified by substitution, deletion, insertion and/or addition of one or more amino acid sequences but still lacks said transmembrane region, binds to CD45, and has immune suppressor activity.

3. The composition according to claim 1, wherein the molecule of interest is an active component.

4. The composition according to claim 3, wherein said active component is an agent used in the prophylaxis or treatment of immune system disorders, autoimmune diseases or hematopoietic malignancies.

5. The composition of claim 3, wherein the active component is selected from the group consisting of a drug or prodrug, a radioactive component, a cytotoxic or apoptosis-inducing component, a cell-proliferation inducing component, a cell-activation inducing component and a cell-differentiation inducing component.

6. The composition according to claim 5, wherein the active component is a cytotoxic or apoptotic inducing component.

7. The composition according to claim 1, wherein said human cytomegalovirus UL11 protein is 95% identical to SEQ ID NO: 2 or SEQ ID NO: 4 and wherein said sequence still lacks said transmembrane region, binds to CD45 and has immune suppressor activity.

8. A composition comprising a nucleic acid encoding i) a recombinant protein comprising at least the extracellular domain of a human cytomegalovirus UL11 protein but not containing the transmembrane region of said human cytomegalovirus UL11 protein, wherein said recombinant protein is able to bind to CD45 and is an immunosuppressor and ii) a heterologous molecule of interest linked with the UL11 domain, and a physiologically acceptable carrier.

* * * * *